United States Patent
Zhu et al.

(10) Patent No.: US 12,221,645 B2
(45) Date of Patent: Feb. 11, 2025

(54) PROCESSES FOR PRODUCING REDUCED COENZYME $Q_{10}$

(71) Applicants: KINGDOMWAY BIOTECHNOLOGY (JIANGSU) CO., LTD., Jiangsu (CN); INNER MONGOLIA KINGDOMWAY PHARMACEUTICAL CO., LTD., Inner Mongolia (CN); JIANGSU CHENGXIN PHARMACEUTICAL CO., LTD., Jiangsu (CN); XIAMEN KINGDOMWAY GROUP COMPANY, Fujian (CN)

(72) Inventors: Jun Zhu, Nantong (CN); Bingrong Wang, Xiamen (CN); Fei Xu, Nantong (CN); Fei Xing, Nantong (CN); Dan Li, Xiamen (CN)

(73) Assignees: KINGDOMWAY BIOTECHNOLOGY (JIANGSU) CO., LTD., Nantong (CN); INNER MONGOLIA KINGDOMWAY PHARMACEUTICAL CO., LTD., Huhhot (CN); JIANGSU CHENGXIN PHARMACEUTICAL CO., LTD., Nantong (CN); XIAMEN KINGDOMWAY GROUP COMPANY, Xiamen (CN)

( * ) Notice: Subject to any disclaimer, the term of this patent is extended or adjusted under 35 U.S.C. 154(b) by 0 days.

(21) Appl. No.: 18/343,727

(22) Filed: Jun. 28, 2023

(65) Prior Publication Data

US 2024/0002891 A1 Jan. 4, 2024

Related U.S. Application Data

(63) Continuation of application No. PCT/CN2023/096228, filed on May 25, 2023.

(51) Int. Cl.
*C12P 7/66* (2006.01)
*C12N 9/02* (2006.01)

(52) U.S. Cl.
CPC .............. *C12P 7/66* (2013.01); *C12N 9/0051* (2013.01); *C12Y 108/01004* (2013.01); *C12Y 108/01007* (2013.01); *C12Y 108/01009* (2013.01)

(58) Field of Classification Search
None
See application file for complete search history.

(56) References Cited

FOREIGN PATENT DOCUMENTS

| CN | 101434971 A | 5/2009 |
| EP | 2314709 A1 | 4/2011 |

OTHER PUBLICATIONS

Xia et al., Eur. J. Biochem. 268, pp. 1486-1490, 2001.*
Matsushita et al., J. Biochem. 105, pp. 633-637, 1989.*
Bjornstedt et al., Methods in Enzmology, vol. 378, pp. 131-138, 2004.*
Yamada et al . . . Journal of Biological Chemistry, vol. 268, No. 17, pp. 12812-12817, 1993.*
Singh et al. (Uniprot Accession No. W8KFM8, May 3, 2023).*
Mauro, Vincent P. et al., A Critical Analysis of Codon Optimization in Human Therapeutics, Trends in Molecular Medicine, 20(11): 604-613, 2014.
"Thioredoxin-disulfide Reductase [Cereibacter sphaeroides]" Genbank accession No. WP_043762649.1, Jan. 28, 2022.
"Dihydrolipoyl Dehydrogenase [Oceanithermus profundus]" Genbank accession No. WP_013458376.1, Jun. 15, 2019.
"Glutathione-disulfide Reductase [Ectothiorhodospira haloalkaliphila]" Genbank accession No. WP_238625258.1, Mar. 1, 2022.
International Search Report in PCT/CN2023/096228 mailed on Feb. 17, 2024, 6 pages.
Written Opinion in PCT/CN2023/096228 mailed on Feb. 17, 2024, 6 pages.

* cited by examiner

*Primary Examiner* — Richard G Hutson
(74) *Attorney, Agent, or Firm* — METIS IP LLC

(57) ABSTRACT

Processes for producing reduced coenzyme $Q_{10}$ ($CoQ_{10}$) are provided. The processes may include preparing a reaction mixture, which includes oxidized $CoQ_{10}$, a reductase, a supplement coenzyme, a coenzyme regeneration enzyme, and a substrate of the coenzyme regeneration enzyme, and providing a condition so that components of the reaction mixture react to produce the reduced $CoQ_{10}$.

11 Claims, 5 Drawing Sheets
Specification includes a Sequence Listing.

100

| Preparing a reaction mixture, which includes oxidized $CoQ_{10}$, a reductase, a supplement coenzyme, a coenzyme regeneration enzyme, and a substrate of the coenzyme regeneration enzyme | 102 |

| Providing a condition so that components of the reaction mixture react to produce the reduced $CoQ_{10}$ | 104 |

```
502
Preparing a plasmid recombinant with a gene
fragment corresponding to the coenzyme regeneration
enzyme
             │
             ▼
504
Obtaining a recombinant strain by transforming a
target strains with the plasmid
             │
             ▼
506
Obtaining a coenzyme regeneration enzyme mix by
culturing the recombinant strain in a culture medium
```

FIG. 5

PROCESSES FOR PRODUCING REDUCED COENZYME $Q_{10}$

CROSS-REFERENCE TO RELATED APPLICATIONS

This application is a Continuation of International Application No. PCT/CN2023/096228, filed on May 25, 2023, the contents of which are incorporated herein by reference in their entirety.

SEQUENCE LISTING

The instant application contains a Sequence Listing which has been submitted electronically in XML format and is hereby incorporated by reference in its entirety. The XML copy, created on Jun. 25, 2023, is named "2023-06-25-Sequence Listing-20605-0004US00" and is 31,277 bytes in size.

TECHNICAL FIELD

The present disclosure generally relates to fermentation engineering, and in particular, to processes for producing reduced coenzyme $Q_{10}$.

BACKGROUND

Coenzyme $Q_{10}$ ($CoQ_{10}$) is a lipid-soluble quinone homolog and mainly has two forms, one is reduced coenzyme $Q_{10}$ (also referred to as ubiquinol), and the other is oxidized coenzyme $Q_{10}$ (also referred to as ubiquinone). Reduced $CoQ_{10}$ is an important respiratory activator and immune enhancer for cell metabolism, having functions such as anti-oxidation, scavenging free radicals, preventing vascular atherosclerosis, and improving chronic respiratory diseases et. al. Reduced $CoQ_{10}$ has been widely used in medicine, health food, food, cosmetics, pharmaceutics, or the like.

At present, the common processes for producing reduced $CoQ_{10}$ employ reducing agents such as sodium hydrosulfite, sodium thiosulfate, sodium borohydride, potassium borohydride, stannous chloride, lithium aluminum hydride, etc. The disadvantages of such processes are that since these reducing agents could affect the quality of the reduced $CoQ_{10}$, a complex approach needs to be implemented to remove them, resulting in higher costs and poorer quality. In addition, the byproduct (Z)-isomer exhibits potential safety hazard but is difficult to remove when it is mixed with the final product. Moreover, due to the large amount of reducing agent needed for the chemical reduction reaction, the whole production process is somewhat dangerous.

Conventionally, reduced $CoQ_{10}$ can also be produced by biological extraction. However, the content of $CoQ_{10}$ in animals and plants is low, the cost is high, and large-scale production is limited.

Therefore, it is desirable to provide processes for producing reducing $CoQ_{10}$ with high yield and purity, low cost, safe in the process, and/or more suitable for industrial production.

SUMMARY

According to the present disclosure, a process for treating producing reduced coenzyme $Q_{10}$ ($CoQ_{10}$) is provided. The process may include preparing a reaction mixture, which includes oxidized $CoQ_{10}$, a reductase, a supplement coenzyme, a coenzyme regeneration enzyme, and a substrate of the coenzyme regeneration enzyme, and providing a condition so that components of the reaction mixture react to produce the reduced $CoQ_{10}$.

In some embodiments, the reductase may include at least one of lipoamide dehydrogenase (LipDH), thioredoxin reductase (TrxR), and glutathione reductase (GR).

In some embodiments, the LipDH may be derived from *Oceanithermus profundus*, and an amino acid sequence of the LipDH has at least 95% similarity with SEQ ID NO: 1.

In some embodiments, the TrxR may be derived from *Cereibacter sphaeroides*, and an amino acid sequence of the TrxR has at least 95% similarity with SEQ ID NO: 2.

In some embodiments, the GR may be derived from *Ectothiorhodospira haloalkaliphila*, and an amino acid sequence of the GR has at least 95% similarity with SEQ ID NO: 3.

In some embodiments, the coenzyme regeneration enzyme may include at least one of glucose dehydrogenase (GDH), formate dehydrogenase (FDH), and alcohol dehydrogenase (ADH).

In some embodiments, the GDH may be derived from *Bacillus subtilis*, and an amino acid sequence of the GDH has at least 95% similarity with SEQ ID NO: 4.

In some embodiments, the FDH may be derived from *Candida boidinii*, and an amino acid sequence of the FDH has at least 95% similarity with SEQ ID NO: 5.

In some embodiments, the ADH may be derived from *Bacillus pseudomycoides*, and an amino acid sequence of the ADH has at least 95% similarity with SEQ ID NO: 6.

In some embodiments, the supplement coenzyme may be $NAD^+$ or $NADP^+$.

In some embodiments, the reaction mixture may be a solution that includes a cosolvent, the cosolvent including at least one of MTBE, n-hexane, n-heptane, toluene, dimethylsulfoxide (DMSO), and ethanol.

In some embodiments, the reaction mixture may further include a metal ion, the metal ion including $Zn^{2+}$ or $Cd^{2+}$.

In some embodiments, the reaction mixture may further include a buffer solution, which includes a Tris-HCl buffer solution, a phosphate buffer solution, triethanolamine hydrochloride, sodium acetate buffer solution, or Tris-phosphate buffer solution.

In some embodiments, a concentration of the oxidized $CoQ_{10}$ in the reaction mixture is at 1%-30%.

In some embodiments, a weight ratio of the reductase to the oxidized $CoQ_{10}$ is in a range of 0.01-1.

In some embodiments, the coenzyme regeneration enzyme may be the GDH, and the substrate may be glucose.

In some embodiments, a weight ratio of the GDH to the oxidized $CoQ_{10}$ is in a range of 0.05-0.25.

In some embodiments, a molar ratio of the glucose to the oxidized $CoQ_{10}$ is in a range of 2-6.

In some embodiments, the coenzyme regeneration enzyme may be the FDH, and the substrate may be ammonium formate.

In some embodiments, a weight ratio of the FDH to the oxidized $CoQ_{10}$ is in a range of 0.05-0.25.

In some embodiments, a molar ratio of the isopropyl alcohol to the oxidized $CoQ_{10}$ is in a range of 2-6.

In some embodiments, a weight ratio of the supplement coenzyme to the oxidized $CoQ_{10}$ is in a range of $10^{-4}$-$10^{-3}$.

In some embodiments, the condition may include that pH of the reaction mixture is maintained in a range of 5.0-8.0.

In some embodiments, the condition may include that a temperate of the reaction mixture is maintained at 25-40° C.

In some embodiments, the condition may include that a reaction time is in a range of 2-24 h.

In some embodiments, the reductase or the coenzyme regeneration enzyme may be prepared by a process including: preparing a plasmid recombinant with a gene fragment corresponding to the reductase or the coenzyme regeneration enzyme; obtaining a recombinant strain by transforming a target strain with the plasmid recombinant with the gene fragment corresponding to the reductase or the coenzyme regeneration enzyme; and obtaining a reductase mix or a coenzyme regeneration enzyme mix by culturing the recombinant strain in a culture medium.

In some embodiments, the gene fragment corresponding to the reductase or the coenzyme regeneration enzyme may be codon optimized.

In some embodiments, one or more nucleotide mutations may be introduced into the gene fragment corresponding to the reductase to generate one or more amino acid substitutions.

In some embodiments, the reductase may be a mutational reductase having an amino acid sequence that has at least 95% similarity with SEQ ID NO: 16, SEQ ID NO: 19, or SEQ ID NO: 22.

In some embodiments, the reductase may be a mutational reductase having an amino acid sequence of SEQ ID NO: 16, SEQ ID NO: 19, or SEQ ID NO: 22.

According to another aspect of the present disclosure, a mutational reductase is provided. In some embodiments, the mutational reductase may have an amino acid sequence that has at least 95% similarity with SEQ ID NO: 16, SEQ ID NO: 19, or SEQ ID NO: 22.

In some embodiments, the mutational reductase may have an amino acid sequence of SEQ ID NO: 16, SEQ ID NO: 19, or SEQ ID NO: 22.

According to another aspect of the present disclosure, a mutational reductase used in a process for producing reduced coenzyme $Q_{10}$ ($CoQ_{10}$) is provided. In some embodiments, the mutational reductase may have one or more amino acid substitutions. In some embodiments, an enzymatic activity of the mutational reductase is at least 1.2 times that of a reductase without mutation.

In some embodiments, the mutational reductase may have an amino acid sequence of the mutational reductase has at least 95% similarity with SEQ ID NO: 16, SEQ ID NO: 19, or SEQ ID NO: 22.

In some embodiments, the mutational reductase may have an amino acid sequence of the mutational reductase is SEQ ID NO: 16, SEQ ID NO: 19, or SEQ ID NO: 22.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein:

FIG. 1 is a flowchart illustrating an exemplary process for producing reduced $CoQ_{10}$ according to some embodiments of the present disclosure;

FIG. 5 is a flowchart illustrating an exemplary process for preparing coenzyme regeneration enzyme according to some embodiments of the present disclosure.

DETAILED DESCRIPTION

Figure 2:
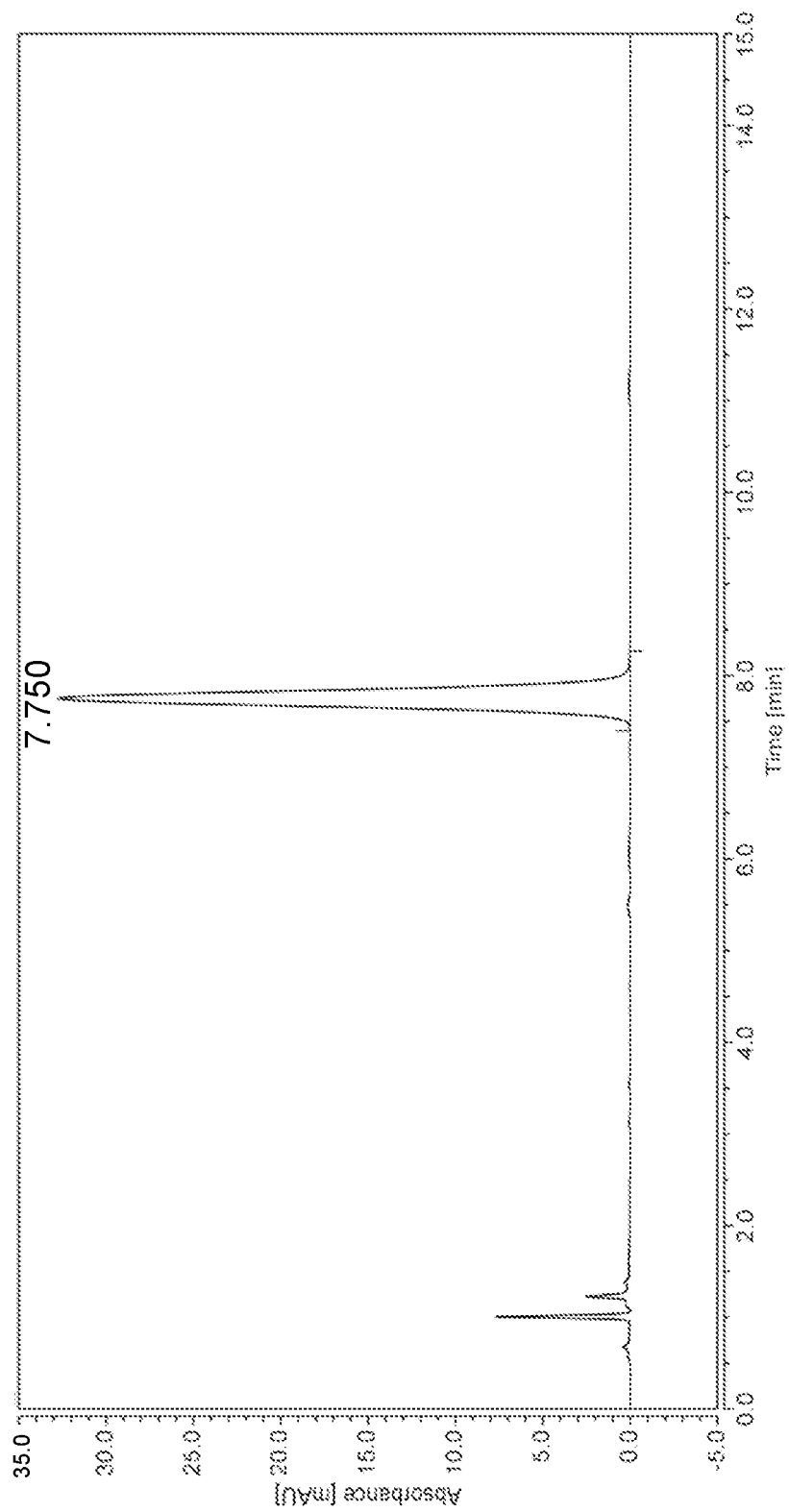
FIG. 2 illustrates a HPLC chromatogram of an oxidized coenzyme $Q_{10}$ ($CoQ_{10}$) according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is to describe particular, example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented in a different order. Conversely, the operations may be implemented in inverted order or simultaneously. Moreover, one or more other operations may be added to the flowcharts. One or more operations may be removed from the flowcharts.

Coenzyme $Q_{10}$ ($CoQ_{10}$) widely exists in organisms and participates in the production of ATP. $CoQ_{10}$ is divided into an oxidized form and a reduced form. Oxidized $CoQ_{10}$ is a fat-soluble quinone, which is orange crystal at room temperature, odorless and tasteless. Oxidized $CoQ_{10}$ is widely distributed in the living world, also referred to as vitamin Q due to its function like a vitamin, and is a component that rejuvenates the body as a nutrient source that brings weak cell activity to a healthy state. The structure of oxidized $CoQ_{10}$ is shown in Formula (I) as follows:

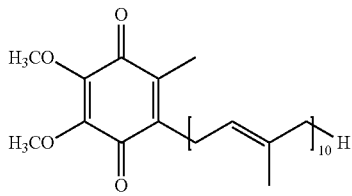

(I)

Reduced $CoQ_{10}$ (also referred to as CoQH) is a natural antioxidant and cell metabolism activator of the cell itself. It has the function of protecting and restoring the integrity of the biological membrane structure, stabilizing the membrane potential, and is a non-specific immune enhancer of the body. Reduced $CoQ_{10}$ is a two-electron reduction form of oxidized $CoQ_{10}$, and oxidized $CoQ_{10}$ is an orange crystal, whereas reduced $CoQ_{10}$ is a white crystal. Reduced $CoQ_{10}$ and oxidized $CoQ_{10}$ are localized in mitochondria, lysosome, golgi apparatus, microsome, peroxisome, cellular membrane and the like, and are indispensable substances for the maintenance of biological functions, which are known to be involved in the activation of ATP production, antioxidant action in the body and stabilization of membrane as a constituent component of the electron transport system. The structure of reduced $CoQ_{10}$ is shown in Formula (II) as follows:

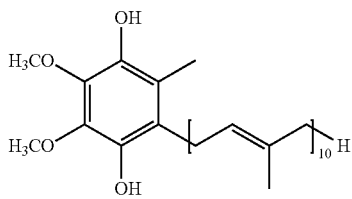

(II)

In the present disclosure, reduced $CoQ_{10}$ may be processed by using a biological enzyme (e.g., a reductase) to simulate the reduction process of oxidized CoQ10 in an organism (e.g., a human body). The reductase may be obtained from a reductase mix which is prepared by a fermentation process of a recombinant strain. The recombinant strain may be an expression host (e.g., *Escherichia coli*) with a vector transformed. The vector is recombinant with the codon-optimized and/or randomly mutated gene fragment corresponding to the reductase. The modified reductase has better activity than the wild type, thereby reducing the usage amount of the reductase and/or accelerating a reaction speed of the reduction process. In addition, a coenzyme regeneration system including a supplement coenzyme ($NAD^+$ or $NADP^+$), a coenzyme regeneration enzyme, and a substrate of the coenzyme regeneration enzyme is constructed in the process to provide NADH or NADPH that is necessary for the reduction reaction, thereby reducing the usage amount of NADH or NADPH and saving cost. The process in the present disclosure is simple, safe, environmentally friendly, and is suitable for industrial production. The reduced $CoQ_{10}$ by such process has high yield and purity, and is easy separated and purified.

FIG. 1 is a flowchart illustrating an exemplary process for producing reduced $CoQ_{10}$ according to some embodiments of the present disclosure.

In 102, a reaction mixture may be prepared.

The reaction mixture contains components which react to produce reduced $CoQ_{10}$ under a condition. The reaction mixture may include oxidized $CoQ_{10}$ and a reductase.

The reductase refers to an enzyme that can convert oxidized $CoQ_{10}$ into reduced $CoQ_{10}$ in the presence of NAD(P)H. In some embodiments, the reductase may include a lipoamide dehydrogenase (LipDH), a thioredoxin reductase (TrxR), and a glutathione reductase (GR), a cytochrome b5 reductase, a ferroptosis suppressor protein 1 (FSP1), or the like, or any combination thereof.

The LipDH is a ubiquitous enzyme which is part of large multienzyme complexes, e.g., a pyruvate dehydrogenase complex. The LipDH can efficiently catalyze the NAD(P) H-dependent one-electron reduction of the oxidized $CoQ_{10}$. In some embodiments, the LipDH may be derived from an organism, including but not limited to a human, an animal, a plant, bacteria, yeast, fungi, or the like, or any combination thereof. For example, the LipDH may be derived from genus *Oceanithermus*, the genus *Streptococcus*, the genus *Bacillus*, the genus *Neurispora*, the genus *Pseudomonas*, the genus *Clostridium*, the genus *Peptostreptococcus*, etc. In some embodiments, the LipDH may be derived from *Oceanithermus profundus*.

In some embodiments, an amino acid sequence of the LipDH may have at least 95% similarity with SEQ ID NO: 1:

```
MYDLIVIGTGPGGYHAAIRAAQLGLKVAAVEAGAVGGVCL

NVGCIPTKALLHAAETLEHAAKGAEFGLVFSEAERDLAKM

GRWRDKIVKKLTGGVASLLKGNGVELVKGFARFTGPRELE

VDGKKLEAKKIIVATGSKPAVLPGFEPDGEHVLTSTEMLR

VENGVPARLLVIGGGVIGLEFASIYARLGAEVTVVEYEGQ

ILPGSDPELVKLLARSLKKQGIVVKTATKAAGYEKAGGGL

RVTVEPAAGGEQEVLDADKILLAVGRVPFTEGLNLEAAGV

RTDERGFVPTNEHLETNVPGVYAIGDVTKPPLLAHKAMKE

GLVAAEHAAGRPAAFDQQIPSVVYTQPEFASVGMTEAEAK

ARGLEVRVGRFPFSASGRALTLQQTEGLIKLVADAENDLL

LGAHILGPGASDLIAEATLALEMAATAGDLALTVHPHPTL

AENLMEAAENLHGRAIHILNR.
```

In some embodiments, the amino acid sequence of LipDH may have at least 96%, 97%, 98%, or 99% similarity with the amino acid sequence shown in SEQ ID NO: 1. In some embodiments, the LipDH has the amino acid sequence shown in SEQ ID NO: 1.

In some embodiments, a nucleotide sequence of the LipDH may have at least 95% similarity with SEQ ID NO: 7:

```
ATGTACGACCTGATTGTGATTGGCACCGGTCCGGGCGGTT

ATCATGCAGCAATTCGCGCCGCCCAGCTGGGTTTAAAAGT

TGCCGCAGTGGAAGCAGGTGCAGTTGGTGGTGTGTGCCTG
```

```
-continued
AATGTGGGTTGCATTCCGACCAAAGCACTGCTGCATGCAG

CCGAAACCCTGGAACATGCCGCCAAAGGCGCAGAATTTGG

CCTGGTTTTTAGCGAAGCAGAACGTGATCTGGCCAAAATG

GGTCGCTGGCGCGATAAAATTGTGAAAAAACTGACCGGTG

GCGTTGCCAGTCTGCTGAAAGGTAATGGTGTGGAACTGGT

TAAAGGCTTTGCACGTTTTACCGGCCCGCGTGAACTGGAA

GTTGATGGTAAAAAACTGGAAGCAAAGAAGATCATCGTGG

CAACCGGTAGTAAACCGGCAGTTCTGCCGGGCTTTGAACC

GGATGGCGAACATGTGCTGACCAGCACCGAAATGCTGCGC

GTGGAAAATGGCGTTCCGGCCAGACTGCTGGTTATTGGTG

GCGGTGTTATTGGTCTGGAATTTGCCAGCATCTATGCACG

CCTGGGTGCAGAAGTGACCGTTGTGGAATATGAAGGCCAG

ATTCTGCCGGGTAGTGATCCGGAACTGGTTAAGCTGCTGG

CCCGTAGCCTGAAAAAACAGGGTATTGTGGTGAAAACCGC

CACCAAAGCAGCCGGTTATGAAAAAGCAGGTGGTGGCCTG

CGTGTGACCGTGGAGCCTGCCGCTGGTGGTGAGCAGGAGG

TGTTAGATGCAGATAAAATTCTGCTGGCCGTTGGCCGCGT

GCCGTTTACCGAGGGTTTAAATCTGGAAGCCGCAGGTGTT

CGCACCGATGAACGTGGTTTTGTTCCGACCAATGAACATC

TGGAAACCAATGTGCCGGGTGTGTATGCAATTGGCGATGT

GACCAAACCGCCGCTGCTGGCACATAAAGCAATGAAAGAA

GGCCTGGTGGCCGCAGAACATGCCGCAGGTAGACCTGCCG

CTTTTGATCAGCAGATTCCGAGTGTGGTTTATACCCAGCC

GGAATTTGCAAGTGTTGGTATGACCGAAGCAGAAGCAAAA

GCCCGTGGCCTGGAAGTGCGTGTGGGTCGTTTTCCGTTTA

GCGCAAGCGGTCGCGCCCTGACCTTACAACAGACCGAAGG

TCTGATTAAGCTGGTTGCAGATGCAGAAAATGATCTGCTG

CTGGGCGCCCATATTCTGGGTCCTGGTGCTAGTGATCTGA

TTGCCGAAGCCACCCTGGCACTGGAAATGGCAGCCACAGC

AGGTGACCTGGCACTGACAGTGCATCCGCATCCGACCCTG

GCAGAAAATCTGATGGAAGCCGCAGAAAATCTTCATGGCC

GTGCAATTCATATTCTGAATCGC.
```

In some embodiments, the nucleotide sequence of LipDH may have at least 96%, 97%, 98%, or 99% similarity with the nucleotide sequence shown in SEQ ID NO: 7. In some embodiments, the LipDH has the nucleotide sequence shown in SEQ ID NO: 7.

TrxR is a reductase that plays an important role in cell proliferation in vitro. TrxR can catalyze the NAD(P)H-dependent reduction of the redox protein thioredoxin (Trx), as well as of other endogenous and exogenous compounds. The TrxR herein is used to catalyze the reduction of oxidized $CoQ_{10}$. In some embodiments, the TrxR may be derived from an organism, including but not limited to a human, an animal, a plant, bacteria, yeast, fungi, or the like, or any combination thereof. For example, the TrxR may be derived from the genus *Escherichia*, the genus *Fusarium*, the genus *Vibrio*, the genus *Cereibacter*, etc. In some embodiments, the TrxR may be derived from *Cereibacter sphaeroides*.

In some embodiments, an amino acid sequence of the TrxR may have at least 95% similarity with SEQ ID NO: 2:

```
MRGKAMAETRHTRVLIIGSGPAGYTAAVYSARAMLNPLLI

QGLQPGGQLTITTEVENWPGDREVQGPELMVRMEDHARAM

GAEIVSDYISSLDLSQRPFTARADSGMTYTADAVILATGA

QARWLGLPSEERFKGFGVSACATCDGFFYRGKEVVVAGGG

NTAVEEALFLTNFASKVTLVHRRDSLRAEKILQDRLFKHP

KIEVLWNHTIEEVAGTEAPLGVTGIVARNVLTGETTEVPC

EGFFVAIGHAPASELVKDQLELHHGGYVRVEPGTTRTSIP

GVFAAGDLTDHVYRQAVTSAGMGCMAALDAERFLAGA.
```

In some embodiments, the amino acid sequence of TrxR may have at least 96%, 97%, 98% or 99% similarity with the amino acid sequence shown in SEQ ID NO: 2. In some embodiments, the TrxR has the amino acid sequence shown in SEQ ID NO: 2.

In some embodiments, a nucleotide sequence of the TrxR may have at least 95% similarity with SEQ ID NO: 8:

```
ATGCGTGGTAAAGCAATGGCAGAAACCCGTCATACCCGTG

TGCTGATTATTGGTAGTGGCCCGGCAGGTTATACCGCCGC

AGTTTATAGTGCACGTGCCATGCTGAATCCGCTGCTGATT

CAGGGTCTGCAACCGGGTGGTCAGCTGACAATTACCACCG

AAGTGGAAAATTGGCCGGGTGACCGTGAAGTGCAGGGCCC

TGAGTTAATGGTTCGTATGGAAGATCATGCCCGCGCAATG

GGTGCCGAAATTGTGAGCGATTATATTAGCAGTCTGGATC

TGAGTCAGCGTCCGTTTACCGCCCGCGCAGATTCAGGTAT

GACCTATACCGCAGATGCCGTTATTCTGGCCACCGGCGCA

CAGGCACGTTGGCTGGGTTTACCTAGCGAAGAACGCTTTA

AAGGCTTTGGCGTTAGTGCCTGTGCCACCTGCGATGGTTT

CTTTTATCGTGGCAAAGAAGTTGTTGTGGCCGGCGGCGGT

AATACCGCTGTTGAAGAAGCACTGTTTCTGACCAATTTTG

CCAGTAAAGTTACCCTGGTGCATCGCCGTGATAGCCTGCG

TGCAGAAAAATTCTGCAAGATCGTCTGTTTAAGCACCCG

AAAATTGAAGTGCTGTGGAATCATACCATCGAAGAAGTTG

CCGGCACCGAAGCACCGCTGGGTGTGACCGGTATTGTTGC

ACGTAATGTTCTGACCGGTGAAACCACCGAAGTTCCGTGC

GAAGGCTTTTCGTGGCCATTGGTCATGCACCGGCCAGCG

AACTGGTGAAAGATCAGCTGGAACTGCATCATGGCGGTTA

TGTGCGTGTGGAACCGGGCACAACCCGTACAAGTATTCCG

GGTGTTTTTGCAGCAGGTGACCTGACCGATCATGTGTATC

GCCAGGCAGTGACCAGTGCCGGTATGGGTTGCATGGCCGC

TCTGGATGCAGAACGCTTTCTGGCAGGCGCATAA.
```

In some embodiments, the nucleotide sequence of TrxR may have at least 96%, 97%, 98% or 99% similarity with the nucleotide sequence shown in SEQ ID NO: 8. In some embodiments, the TrxR has the nucleotide sequence shown in SEQ ID NO: 8.

GR is a ubiquitous 100-120 kDa dimeric flavoprotein encoded by the GSR gene and can catalyze the reduction of oxidized glutathione (GSSG) to reduced glutathione (GSH). The GR herein is used to catalyze the NADH or NADPH-dependent reduction of oxidized $CoQ_{10}$. In some embodiments, the GR may be derived from an organism, including but not limited to a human, an animal, a plant, bacteria, yeast, fungi, or the like, or any combination thereof. For example, the GR may be derived from the genus *Ectothiorhodospira*, the genus *Escherichia*, etc. In some embodiments, the GR may be derived from *Ectothiorhodospira shaposhnikovii*.

In some embodiments, an amino acid sequence of the GR may have at least 95% similarity with SEQ ID NO: 3:

```
MNDHYDLIAIGAGSGGLSVVERAARYGALCAVVESGPLGG

TCVNVGCVPKKVMWYAADMAHRLDDAPGYGFKLAREGFDW

SELVGARDAYIEGINTWYHTYLADSGVDEIPGRARFVDAH

TLEVDGRRVSADHVVIAVGGQPSVPDIPGAELGITSDGFF

QLKSQPRRVAVIGAGYIAVELAGMLRALGSEVSMYLRRQT

LLRSFDPMLRDTLMEQMLADGVNLFPSTQVGRLIAHPDSV

ELFCDQGECRGVFDQVIWATGRTPATNDLDLHNTGIQPDD

QGYIPTDLYQNTSVEGVYAIGDVTGRAPLTPVAIAAGRRL

ADRLFGGQTDRHLSYETIPSVIFSHPPIGTVGLTEEEARA

AHGEAVKVYSTRFTSMYHAMTPHKVATAMKLVTVGAQEKV

VGVHIIGPDADEMLQGFAVAVRMGATKRDLDDTVALHPTS

AEELVTMK.
```

In some embodiments, the amino acid sequence of GR may have at least 96%, 97%, 98% or 99% similarity with the amino acid sequence shown in SEQ ID NO: 3. In some embodiments, the GR has the amino acid sequence shown in SEQ ID NO: 3.

In some embodiments, a nucleotide sequence of the GR may have at least 95% similarity with SEQ ID NO: 9:

```
ATGAACGACCATTACGATCTGATTGCAATTGGTGCCGGTA

GCGGTGGCCTGTCAGTTGTTGAACGCGCCGCACGTTATGG

CGCCTTATGTGCAGTTGTGGAAAGCGGCCCGCTGGGTGGT

ACATGTGTGAATGTGGGCTGTGTTCCGAAAAAAGTGATGT

GGTATGCAGCCGATATGGCACATCGCCTGGATGATGCCCC

GGGTTATGGCTTTAAACTGGCACGTGAAGGTTTTGATTGG

AGTGAACTGGTTGGCGCCCGTGATGCCTATATTGAAGGCA

TTAATACCTGGTATCACACCTATCTGGCCGATAGCGGCGT

GGATGAAATTCCGGGTCGTGCACGCTTTGTGGATGCACAT

ACCCTGGAAGTGGATGGCCGTCGTGTGAGCGCAGATCATG

TTGTGATTGCCGTGGGCGGTCAGCCGAGTGTTCCTGACAT
```

```
TCCGGGTGCCGAACTGGGTATTACCAGCGATGGCTTTTTC

CAGCTGAAAAGCCAGCCGCGCCGTGTTGCAGTGATTGGTG

CTGGTTATATTGCAGTGGAACTGGCCGGCATGCTGCGCGC

ATTAGGTAGTGAAGTGAGCATGTATCTGCGCCGTCAGACC

CTGCTGCGCAGTTTTGATCCGATGCTGCGTGATACCCTGA

TGGAACAGATGCTGGCAGATGGCGTTAATCTGTTTCCGAG

TACCCAGGTTGGTCGTCTGATTGCCCATCCGGATAGCGTG

GAACTGTTTTGCGATCAGGGCGAATGCCGTGGTGTTTTTG

ATCAGGTTATTTGGGCAACCGGTCGCACCCCGGCAACAAA

TGATCTGGATCTGCATAATACCGGTATTCAGCCGGATGAT

CAGGGTTATATTCCGACCGATCTGTATCAGAATACCAGTG

TGGAAGGCGTGTATGCCATTGGTGACGTTACCGGCCGTGC

CCCTCTGACCCCTGTGGCAATCGCAGCAGGTCGTCGTCTG

GCAGATCGTCTGTTTGGTGGTCAGACCGATCGCCATCTGA

GCTATGAAACCATTCCGAGTGTGATTTTTAGCCATCCGCC

GATTGGTACAGTTGGCCTGACCGAAGAAGAAGCACGCGCC

GCACATGGTGAAGCAGTTAAAGTTTATAGCACCCGTTTTA

CCAGTATGTATCATGCCATGACCCCGCATAAAGTTGCAAC

CGCCATGAAACTGGTGACCGTGGGCGCACAGGAAAAAGTG

GTGGGTGTTCATATTATTGGTCCGGATGCAGATGAAATGC

TGCAAGGCTTTGCCGTTGCCGTTCGCATGGGCGCAACCAA

ACGTGATCTGGATGATACCGTGGCACTGCATCCGACCAGC

GCAGAAGAACTGGTGACCATGAAATAA.
```

In some embodiments, the nucleotide sequence of GR may have at least 96%, 97%, 98% or 99% similarity with the nucleotide sequence shown in SEQ ID NO: 9. In some embodiments, the GR has the nucleotide sequence shown in SEQ ID NO: 9.

In some embodiments, the gene sequences of the LipDH, TrxR, and GR may be modified to enhance the reduction ability. For example, the gene sequences of the LipDH, TrxR, and GR may be modified by gene engineering. Merely by way of example, one or more nucleotides of each reductase may be added, deleted, and/or substituted; the gene sequences of the LipDH, TrxR, and GR may be recombined with strong promoters to increase gene expression. As another example, other biological techniques (e.g., chemically induced mutation, random mutagenesis) may be applied to these enzymes to improve reduction function. In some embodiments, gene fragments encoding the amino acid sequences of the LipDH, TrxR, and GR may be codon optimized to enhance protein expression. In some embodiments, the LipDH, TrxR, and GR may be obtained through a fermentation process of a recombinant strain. More description about the obtaining LipDH, TrxR, and GR can be found in FIG. 4 and description thereof.

In some embodiment, the reductase may be a mutational reductase. The mutational reductase may have an amino acid sequence that has at least 95%, 96%, 97%, 98%, or 99% similarity with SEQ ID NO: 16. In some embodiment, the mutational reductase may have an amino acid sequence that has at least 95%, 96%, 97%, 98%, or 99% similarity with SEQ ID NO: 19. In some embodiment, the mutational reductase may have an amino acid sequence that has at least 95%, 96%, 97%, 98%, or 99% similarity with SEQ ID NO: 22. In some embodiment, the mutational reductase may have an amino acid sequence of SEQ ID NO: 16, SEQ ID NO: 19, or SEQ ID NO: 22.

The reaction mixture may further include a supplement coenzyme, a coenzyme regeneration enzyme, and a substrate of the coenzyme regeneration enzyme, which constitute a coenzyme regeneration system to continuously provide reduced coenzyme (e.g., NADH, NADPH) that is necessary for the reduction reaction of oxidated $CoQ_{10}$. The reduction reaction may further generate the coenzyme ($NAD^+$, $NADP^+$) which can be used in coenzyme regeneration reaction. Thus, only small amount of supplement coenzyme can be used, the coenzyme can be continuously provided, thereby saving the usage amount of coenzyme.

The supplement coenzyme is a coenzyme that is added in the reaction mixture to start the coenzyme regeneration reaction. In some embodiments, the coenzyme is an organic molecule that binds to an active site of the enzyme (i.e., the reductase) to assist in the catalysis of the reduction reaction. Specifically, the coenzyme can function as intermediate carriers of electrons during the reduction reaction. In some embodiments, the supplement coenzyme may be $NAD^+$ or $NADP^+$ since the reductase can function with either NADH or NADPH as hydrogen donor. In some embodiments, the supplement coenzyme may be other coenzymes (e.g., FAD, FMN), which are not limited herein.

The coenzyme regeneration enzyme can be applied in the transformation with an $NAD^+$ or $NADP^+$-dependent reaction to achieve the regeneration of the consumed coenzyme. In some embodiments, the coenzyme regeneration enzyme may include glucose dehydrogenase (GDH), formate dehydrogenase (FDH), and alcohol dehydrogenase (ADH), glyceraldehyde 3-phosphate dehydrogenase, succinate dehydrogenase, isocitrate dehydrogenase, malate dehydrogenase, glucose 6-phosphate dehydrogenase, L-glutamate dehydrogenase, acetaldehyde dehydrogenase, or the like, or any combination thereof. Not all the coenzyme regeneration enzymes can reduce both $NAD^+$ and $NADP^+$. For example, the GDH can reduce both $NAD^+$ and $NADP^+$. As another example, the ADH is either $NAD^+$- or $NADP^+$-specific. ADH from horse liver, for example, reduces $NAD^+$ while ADH from Lactobacillus strains catalyzes the reduction of $NADP^+$.

Different coenzyme regeneration enzymes may react with different substrates to achieve coenzyme regeneration. Taking GDH, FDH, and ADH as examples to illustrate the reaction process. GDH and glucose, the substrate of GDH, may be used to establish the $NAD^+$/NADH or $NADP^+$/NADPH regeneration system (shown in formula (A)). GDH catalyzes the oxidation of glucose in the presence of $NAD^+$ or $NADP^+$ to generate gluconic acid, NADH or NADPH, etc.

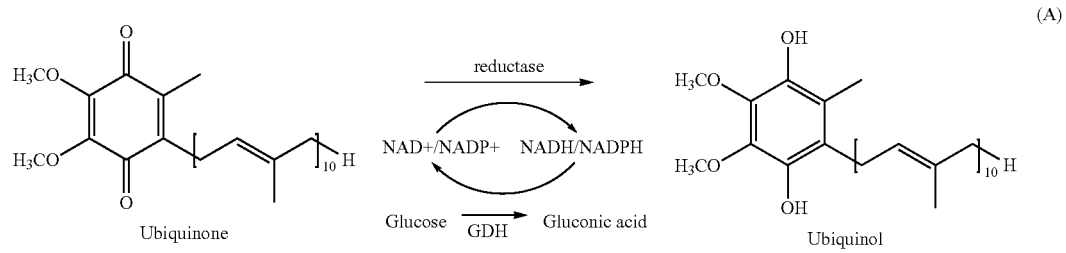

FDH and ammonium formate, a substrate of FDH, may be used to establish the $NAD^+$/NADH or $NADP^+$/NADPH regeneration system. FDH can catalyze the oxidation of the ammonium formate to carbon dioxide, coupled with NAD+ or NADP+ reduction to generate NADH or NADPH (shown in formula (B)).

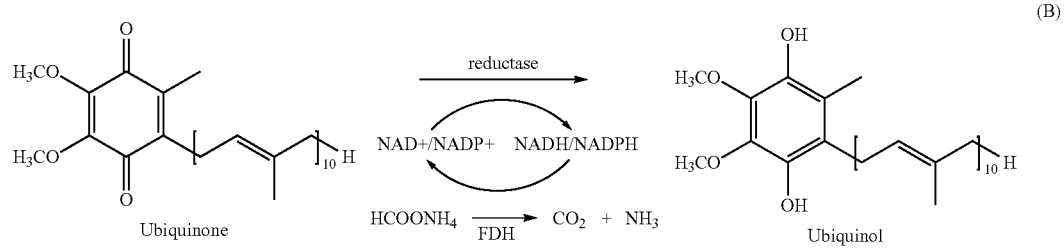

The coenzyme regeneration system is to continually regenerate coenzyme from the oxidated form to the reduced form, so as to keep the coenzyme at a certain level in the reaction mixture. Further, the regenerated coenzyme (i.e., NADH or NADPH) can continuously participant in the reduction reaction for generating the reduced $CoQ_{10}$.

ADH and isopropanol (also referred to as 2-propanol, isopropyl alcohol), the substrate of the ADH, may be used to establish the $NAD^+$/NADH or $NADP^+$/NADPH regeneration system (shown in formula (C)). ADH catalyzes the oxidation of isopropanol in the presence of $NAD^+$ or $NADP^+$ to generate acetone, NADH or NADPH, etc.

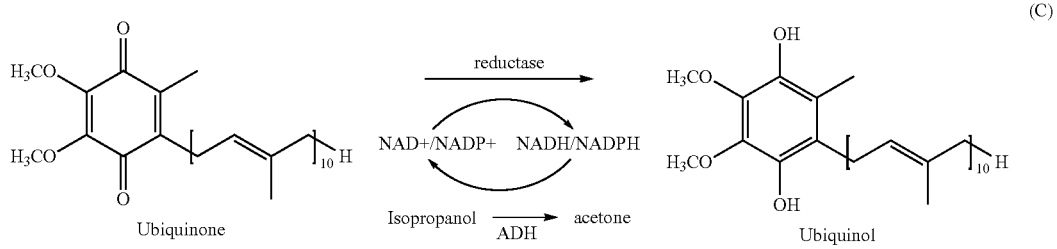

The NADH/NADPH generated by the coenzyme regeneration system may be participant in the reduction reaction of oxidated CoQ10 without adding extra NADH/NADPH, which can effectively reduce the use amount of NADH or NADPH and according effectively reduce the production cost. Moreover, the enzyme-catalyzed reaction is carried out in vitro, the process is simple, and the industrial production is easy to be implemented.

In some embodiments, the GDH may be derived from an organism, including but not limited to a human, an animal, a plant, bacteria, yeast, fungi, or the like, or any combination thereof. For example, the GDH be derived from the genus *Penicillium*, the genus *Bacillus*, the genus *Escherichia*, etc. In some embodiments, the GDH may be derived from *Bacillus subtilis*.

In some embodiments, an amino acid sequence of the GDH may have at least 95% similarity with SEQ ID NO: 4:

```
MYPDLKGKWVAITGAASGLGKAMAIRFGKEQAKVVINYYS

NKQDPNEVKEEVIKAGGEAVVVQGDVTKEEDVKNIVQTAI

KEFGTLDIMINNAGLENPVPSHEMPLKDWDKVIGTNLTGA

FLGSREAIKYFVENDIKGNVINMSSVHEVIPWPLFVHYAA

SKGGIKLMTETLALEYAPKGIRVNNIGPGAINTPINAEKF

ADPKQKADVESMIPMGYIGEPEEIAAVAAWLASKEASYVT

GITLFADGGMTKYPSFQAGRG.
```

In some embodiments, the amino acid sequence of GDH may have at least 96%, 97%, 98% or 99% similarity with the amino acid sequence shown in SEQ ID NO: 4. In some embodiments, the GDH has the amino acid sequence shown in SEQ ID NO: 4.

In some embodiments, the FDH may be derived from an organism including but not limited to a human, an animal, a plant, bacteria, yeast, fungi, or the like, or any combination thereof. For example, the FDH may be derived from the genus *Candida*, the genus *Pichia*, the genus *Hansenula*, the genus *Pseudomonas*, the genus *Moraxella*, the genus *Mycobacterium*, the genus *Paracoccus*, the genus *Ancylobacter*, the genus *ThioBacillus* and the genus *Torulopsis*. In some embodiments, the FDH may be derived from *Candida boidinii*.

In some embodiments, an amino acid sequence of the FDH may have at least 95% similarity with SEQ ID NO: 5:

```
MKIVLVLYDAGKHAADEEKLYGCTENKLGIANWLKDQGHE

LITTSDKEGETSELDKHIPDADIIITTPFHPAYITKERLD

KAKNLKLVVVAGVGSDHIDLDYINQTGKKISVLEVTGSNV

VSVAEHVVMTMLVLVRNFVPAHEQIINHDWEVAAIAKDAY

DIEGKTIATIGAGRIGYRVLERLLPFNPKELLYYDYQALP

KEAEEKVGARRVENIEELVAQADIVTVNAPLHAGTKGLIN

KELLSKFKKGAWLVNTARGAICVAEDVAAALESGQLRGYG

GDVWFPQPAPKDHPWRDMRNKYGAGNAMTPHYSGTTLDAQ

TRYAEGTKNILESFFTGKFDYRPQDIILLNGEYVTKAYGK

HDKK.
```

In some embodiments, the amino acid sequence of FDH may have at least 96%, 97%, 98% or 99% similarity with the amino acid sequence shown in SEQ ID NO: 5. In some embodiments, the FDH has the amino acid sequence shown in SEQ ID NO: 5.

In some embodiments, the ADH may be derived from an organism, including but not limited to a human, an animal, a plant, bacteria, yeast, fungi, or the like, or any combination thereof. For example, the ADH be derived from the genus *Bacillus*, the genus *Escherichia*, the genus Lactobacillus, etc. In some embodiments, ADH may be derived from *Bacillus pseudomycoides*.

In some embodiments, an amino acid sequence of the ADH may have at least 95% similarity with SEQ ID NO: 6:

```
MKAAVVNEFKEKLEVKEVPKPKAELGEVLVHIEACGVCHT

DLHAAHGDWPVKPKLPLIPGHEGVGVIEEVGEGVTHVKVG

DRVGVPWLYSACGHCEYCLSGRETLCLDQHNAGYSVDGGY

AEYCVAAADYVVKVPDNLEFVDAAPLFCAGVTTYKALKVS

EAKPGDWVAIFGIGGLGHLAVQYAKAMGLHVVAVDTVDDK

LELAKELGADLAVNPLKEDAAAWIFEKVKGVHASICTAVS

KPAFDQAYRSVRRGGACVAVGLPPEMMEVPIFDTVLNGVK

IIGSIVGTRKDLQETLQFAAEGKVKAIIETRHLDEINEIF

SEMEEGKINGRVVLDMTK.
```

In some embodiments, the amino acid sequence of ADH may have at least 96%, 97%, 98% or 99% similarity with the amino acid sequence shown in SEQ ID NO: 6. In some embodiments, the ADH has the amino acid sequence shown in SEQ ID NO: 6.

In some embodiments, the gene sequences of the GDH, FDH, and ADH may be modified to enhance the coenzyme regeneration ability. For example, the gene sequences of the GDH, FDH, and ADH may be modified by gene engineering. Merely by way of example, one or more nucleotides of each enzyme may be added, deleted, and/or substituted; the gene sequences of the GDH, FDH, and ADH may be recombined with strong promoters to increase gene expression. As another example, other biological techniques (e.g., chemically induced mutation) may be applied to these enzymes to improve coenzyme regeneration function. In some embodiments, gene fragments encoding the amino acid sequences of the GDH, FDH, and ADH may be codon optimized to enhance protein expression. The GDH, FDH, and ADH may be obtained through a fermentation process of a recombinant strain. More description about the obtaining GDH, FDH, and ADH can be found in FIG. 5 and description thereof.

In some embodiments, the reaction mixture is a solution that includes a cosolvent. The cosolvent may be used to dissolve oxidized $CoQ_{10}$. The cosolvent may include at least one of n-hexane, 2-methylbutane, cyclopentane, n-hexane, 2-methylpentane, 2,2-dimethylbutane, 2,3-dimethylbutane, methylcyclopentane, cyclohexane, THF, n-heptane, 2-methylhexane, 3-methylhexane, 2,3-dimethylpentane, 2,4-dimethylpentane, methylcyclohexane, octane, 2,2,3-trimethylpentane, isooctane, ethylcyclohexane, 1-octene, isopropyl ether, acetone, ethyl acetate, butanone, dichloromethane, methyl acetate, ethyl acetate, propyl acetate, isopropyl acetate, butyl acetate, methyl propionate, methyl tert-butyl ether (MTBE), ethyl propionate, butyl propionate, diethyl ether, methylethylketone, methanol, n-propanol, isopropanol, n-butanol, isobutanol, acetonitrile, toluene, dimethylsulfoxide (DMSO). In some embodiments, the cosolvent may include at least one of MTBE, n-hexane, n-heptane, toluene, dimethylsulfoxide (DMSO), ethanol. The cosolvent used herein can increase the solubility of oxidized $CoQ_{10}$ since it has poor water solubility, and thus improve the yield of reduced $CoQ_{10}$.

Additionally or alternatively, the reaction mixture may include a metal ion. Metal ions can stabilize the conformation of enzymes, participate in catalytic reactions, transfer electrons, and thus improve the catalytic effect of enzymatic reactions (e.g., increase the reaction speed and short the reaction time). The metal ions may include but not limited to $Mg^{2+}$, $Zn^{2+}$, $Mn^{2+}$, $Co^{2+}$, $Cd^{2+}$, $Ca^{2+}$, or the like, or any combination thereof. In some embodiments, the metal ion may include $Zn^{2+}$ or $Cd^{2+}$. It should be noted that the metal ion may be omitted if the reaction time is long enough.

In some embodiments, the reaction mixture may further include a buffer (or referred to as buffer solution) as a solvent. The buffer may include but not limited to Sodium Phosphate Buffer (PBNa), Potassium Phosphate Buffer, ammonium sulphate, tris-(hydroxymethyl)-aminomethane (Tris), 3-(N-morpholino) propanesulfonic Acid (MOPS), 2-[4-(2-Hydroxyethyl)-1-piperazinyl] ethanesulfonic acid (HEPES), phosphate buffer saline (PBS), Tris-hydrochloride (Tris-HCl), triethanolamine hydrochloride, sodium acetate or Tris-phosphate. In some embodiments, the buffer is PBNa or Tris-HCl.

In 104, a condition may be provided so that components of the reaction mixture react to produce the reduced $CoQ_{10}$.

In some embodiments, a concentration of the oxidized $CoQ_{10}$ in the reaction mixture may be at 1%-30%. In some embodiments, a concentration of the oxidized $CoQ_{10}$ in the reaction mixture may be at 3%-30%. In some embodiments, a concentration of the oxidized $CoQ_{10}$ in the reaction mixture may be at 3%-28%. In some embodiments, a concentration of the oxidized $CoQ_{10}$ in the reaction mixture may be at 3%-25%. In some embodiments, a concentration of the oxidized $CoQ_{10}$ in the reaction mixture may be at 3%-23%. In some embodiments, a concentration of the oxidized $CoQ_{10}$ in the reaction mixture may be at 3%-20%. In some embodiments, a concentration of the oxidized $CoQ_{10}$ in the reaction mixture may be at 5%-20%. In some embodiments, a concentration of the oxidized $CoQ_{10}$ in the reaction mixture may be at 5%-18%. In some embodiments, a concentration of the oxidized $CoQ_{10}$ in the reaction mixture may be at 6%-15%. In some embodiments, a concentration of the oxidized $CoQ_{10}$ in the reaction mixture may be at 6%-12%. In some embodiments, a concentration of the oxidized $CoQ_{10}$ in the reaction mixture may be at 1%, 3%, 5%, 6%, 10%, 12%, 15%, 20%, 25%, 28%, or 30%.

In some embodiments, a weight ratio of the reductase to the oxidized $CoQ_{10}$ is in a range of 0.01-1. In some embodiments, a weight ratio of the reductase to the oxidized $CoQ_{10}$ is in a range of 0.025-0.5. In some embodiments, a weight ratio of the reductase to the oxidized $CoQ_{10}$ is in a range of 0.05-0.5. In some embodiments, a weight ratio of the reductase to the oxidized $CoQ_{10}$ is in a range of 0.1-0.5. In some embodiments, a weight ratio of the reductase to the oxidized $CoQ_{10}$ is in a range of 0.125-0.375. In some embodiments, a weight ratio of the reductase to the oxidized $CoQ_{10}$ is 0.01, 0.025, 0.05, 0.1, 0.125, 0.2, 0.25, 0.375, 0.4, 0.5, or 1. In some embodiments, a weight ratio of the reductase to the coenzyme regeneration enzyme is 0.25. In some embodiments, a weight ratio of the reductase to the oxidized $CoQ_{10}$ is 0.125.

In some embodiments, a weight ratio of the GDH to oxidized $CoQ_{10}$ is in a range of 0.03-0.3. In some embodiments, a weight ratio of the GDH to oxidized $CoQ_{10}$ is in a range of 0.05-0.25. In some embodiments, a weight ratio of the GDH to oxidized $CoQ_{10}$ is in a range of 0.05-0.2. In some embodiments, a weight ratio of the GDH to oxidized $CoQ_{10}$ is in a range of 0.1-0.25. In some embodiments, a weight ratio of the GDH to oxidized $CoQ_{10}$ is in a range of 0.1-0.2. In some embodiments, a weight ratio of the GDH to oxidized $CoQ_{10}$ is in a range of 0.1-0.15. In some embodiments, a weight ratio of the GDH to oxidized $CoQ_{10}$ is 0.05, 0.1, 0.15, 0.2, or 0.25 In some embodiments, a weight ratio of the GDH to oxidized $CoQ_{10}$ is 0.125.

In some embodiments, a molar ratio of the glucose to oxidized $CoQ_{10}$ is in a range of 2-8. In some embodiments, a molar ratio of the glucose to oxidized $CoQ_{10}$ is in a range of 2-6. In some embodiments, a molar ratio of the glucose to oxidized $CoQ_{10}$ is in a range of 3-6. In some embodiments, a molar ratio of the glucose to oxidized $CoQ_{10}$ is in a range of 4-6. In some embodiments, a molar ratio of the glucose to oxidized $CoQ_{10}$ is in a range of 5-6. In some embodiments, a molar ratio of the glucose to oxidized $CoQ_{10}$ is in a range of 2-5. In some embodiments, a molar ratio of the glucose to oxidized $CoQ_{10}$ is in a range of 2-4. In some embodiments, a molar ratio of the glucose to oxidized $CoQ_{10}$ is in a range of 2-3. In some embodiments, a molar ratio of the glucose to oxidized $CoQ_{10}$ is 2, 3, 4, 5, or 6.

In some embodiments, a weight ratio of the FDH to oxidized $CoQ_{10}$ is in a range of 0.03-0.3. In some embodiments, a weight ratio of the FDH to oxidized $CoQ_{10}$ is in a range of 0.05-0.25. In some embodiments, a weight ratio of the FDH to oxidized $CoQ_{10}$ is in a range of 0.05-0.2. In some embodiments, a weight ratio of the FDH to oxidized $CoQ_{10}$ is in a range of 0.05-0.1. In some embodiments, a weight ratio of the FDH to oxidized $CoQ_{10}$ is in a range of 0.05-0.2. In some embodiments, a weight ratio of the FDH to oxidized $CoQ_{10}$ is in a range of 0.1-0.2. In some embodiments, a weight ratio of the FDH to oxidized $CoQ_{10}$ is in a range of 0.15-0.2. In some embodiments, a weight ratio of the GDH to oxidized $CoQ_{10}$ is 0.05, 0.1, 0.15, 0.2, or 0.25. In some embodiments, a weight ratio of the GDH to oxidized $CoQ_{10}$ is 0.1875.

In some embodiments, a molar ratio of the ammonium formate to oxidized $CoQ_{10}$ is in a range of 2-8. In some embodiments, a molar ratio of the ammonium formate to oxidized $CoQ_{10}$ is in a range of 2-6. In some embodiments, a molar ratio of the ammonium formate to oxidized $CoQ_{10}$ is in a range of 3-6. In some embodiments, a molar ratio of the ammonium formate to oxidized $CoQ_{10}$ is in a range of 4-6. In some embodiments, a molar ratio of the ammonium formate to oxidized $CoQ_{10}$ is in a range of 5-6. In some embodiments, a molar ratio of the ammonium formate to oxidized $CoQ_{10}$ is in a range of 2-5. In some embodiments, a molar ratio of the the ammonium formate to oxidized $CoQ_{10}$ is in a range of 2-4. In some embodiments, a molar ratio of the ammonium formate to oxidized $CoQ_{10}$ is in a range of 2-3. In some embodiments, a molar ratio of the ammonium formate to oxidized CoQ10 is 2, 3, 4, 5, or 6.

In some embodiments, a weight ratio of the ADH to oxidized $CoQ_{10}$ is in a range of 0.03-0.3. In some embodiments, a weight ratio of the ADH to oxidized $CoQ_{10}$ is in a range of 0.05-0.25. In some embodiments, a weight ratio of the ADH to oxidized $CoQ_{10}$ is in a range of 0.05-0.2. In some embodiments, a weight ratio of the ADH to oxidized $CoQ_{10}$ is in a range of 0.05-0.1. In some embodiments, a weight ratio of the ADH to oxidized $CoQ_{10}$ is in a range of 0.05-0.2. In some embodiments, a weight ratio of the ADH to oxidized $CoQ_{10}$ is in a range of 0.1-0.2. In some embodiments, a weight ratio of the ADH to oxidized $CoQ_{10}$ is in a range of 0.15-0.2. In some embodiments, a weight ratio of the ADH to oxidized $CoQ_{10}$ is 0.05, 0.1, 0.15, 0.1875, 0.2, or 0.25.

In some embodiments, a molar ratio of the isopropanol to oxidized $CoQ_{10}$ is in a range of 2-8. In some embodiments, a molar ratio of the isopropanol to oxidized $CoQ_{10}$ is in a range of 2-6. In some embodiments, a molar ratio of the isopropanol to oxidized $CoQ_{10}$ is in a range of 3-6. In some embodiments, a molar ratio of the isopropanol to oxidized $CoQ_{10}$ is in a range of 4-6. In some embodiments, a molar ratio of the isopropanol to oxidized $CoQ_{10}$ is in a range of 5-6. In some embodiments, a molar ratio of the isopropanol to oxidized $CoQ_{10}$ is in a range of 2-5. In some embodiments, a molar ratio of the isopropanol to oxidized $CoQ_{10}$ is in a range of 2-4. In some embodiments, a molar ratio of the isopropanol to oxidized $CoQ_{10}$ is in a range of 2-3. In some embodiments, a molar ratio of the isopropanol to oxidized CoQ10 is 2, 3, 4, 5, or 6.

In some embodiments, a weight ratio of the supplement coenzyme to the oxidized $CoQ_{10}$ is in a range of $10^{-4}$–$10^{-3}$. In some embodiments, a weight ratio of the supplement coenzyme to the oxidized $CoQ_{10}$ is in a range of $2\times10^{-4}$–$10^{-3}$. In some embodiments, a weight ratio of the supplement coenzyme to the oxidized $CoQ_{10}$ is in a range of $3\times10^{-4}$–$10^{-3}$. In some embodiments, a weight ratio of the supplement coenzyme to the oxidized $CoQ_{10}$ is in a range of $5\times10^{-4}$–$10^{-3}$. In some embodiments, a weight ratio of the supplement coenzyme to the oxidized $CoQ_{10}$ is in a range of $6\times10^{-4}$–$10^{-3}$.

In some embodiments, the volume ratio of the co-solvent to the buffer is 0.03-0.7. In some embodiments, the volume ratio of the co-solvent to the buffer is 0.05-0.5. In some embodiments, the volume ratio of the co-solvent to the buffer is 0.1-0.3. In some embodiments, the volume ratio of the co-solvent to the buffer is 0.05, 0.1, 0.2, 0.3, 0.4, or 0.5. In some embodiments, the volume ratio of the co-solvent to the buffer is 0.2.

In some embodiments, the condition for the reaction may include that pH of the reaction mixture is maintained in a range of 4.0-9.0. In some embodiments, the condition includes that pH of the reaction mixture is maintained in a range of 5.0-8.0. In some embodiments, the condition may include that pH of the reaction mixture is maintained in a range of 6.0-7.5. In some embodiments, the condition includes that pH of the reaction mixture is maintained at 5.0, 5.5, 6.0, 6.5, 6.8, 7.0, 7.5 or 8.0.

In some embodiments, the condition includes that a temperate of the reaction mixture is maintained at 22-45° C. In some embodiments, the condition includes that a temperate of the reaction mixture is maintained at 24-43° C. In some embodiments, the condition includes that a temperate of the reaction mixture is maintained at 25-40° C. In some embodiments, the condition includes that a temperate of the reaction mixture is maintained at 25° C., 28° C., 30° C. 35° C., 37° C., or 40° C. In some embodiments, the condition includes that a temperate of the reaction mixture is maintained at 37° C.

In some embodiments, the condition includes that a reaction time is in a range of 2-48 h. In some embodiments, the condition includes that a reaction time is in a range of 2-24 h. In some embodiments, the condition includes that a reaction time is in a range of 4-24 h. In some embodiments, the condition includes that a reaction time is in a range of 12-24 h. In some embodiments, the condition includes that a reaction time is 2 h, 4 h, 8 h, 12 h, or 24 h.

The reduced $CoQ_{10}$ prepared by the above process can achieve the high purity, for example, higher than or equal to 98%, 98.5%, 99%, or 99.5%. The purity of the reduced $CoQ_{10}$ may be determined by the level of reduced $CoQ_{10}$ and oxidized $CoQ_{10}$. In some embodiments, the level of reduced $CoQ_{10}$ and oxidized $CoQ_{10}$ may be monitored according to a qualitative analysis method. Exemplary qualitative analysis method for monitoring the presence of reduced $CoQ_{10}$ and oxidized $CoQ_{10}$ may include liquid chromatography (LC), high performance liquid chromatography (HPLC), thin-layer chromatography (TLC), liquid chromatography-mass spectroscopy (LC-MS), or the like, or a combination thereof. Taking HPLC as an example to detect the level of reduced $CoQ_{10}$ and oxidized $CoQ_{10}$, 1 mL of a sample was added into methanol: n-hexane (85%:15%) solution at the ratio of 1:9, mixed evenly, and filtered by a 0.22 μm filter membrane; 20 μL of a filtrate was taken for HPLC analysis. The chromatographic conditions were as follows:

Chromatographic column: Agilent $C_{18}$, 4.6×100 mm, 3.5-Micron.
Mobile phase: consisted of acetonitrile and ethanol (with a volume ratio of 50%:50%).
Temperature: 35° C.
Speed of mobile phase: 1.5 mL/min.
Detection wavelength: 290 nm.

The purity of reduced $CoQ_{10}$ is calculated by the following formula:

The purity of reduced $CoQ_{10}$(%)=peak area of reduced $CoQ_{10}$/(peak area of reduced $CoQ_{10}$+ peak area of other components)×100%     (1).

Figure 3:
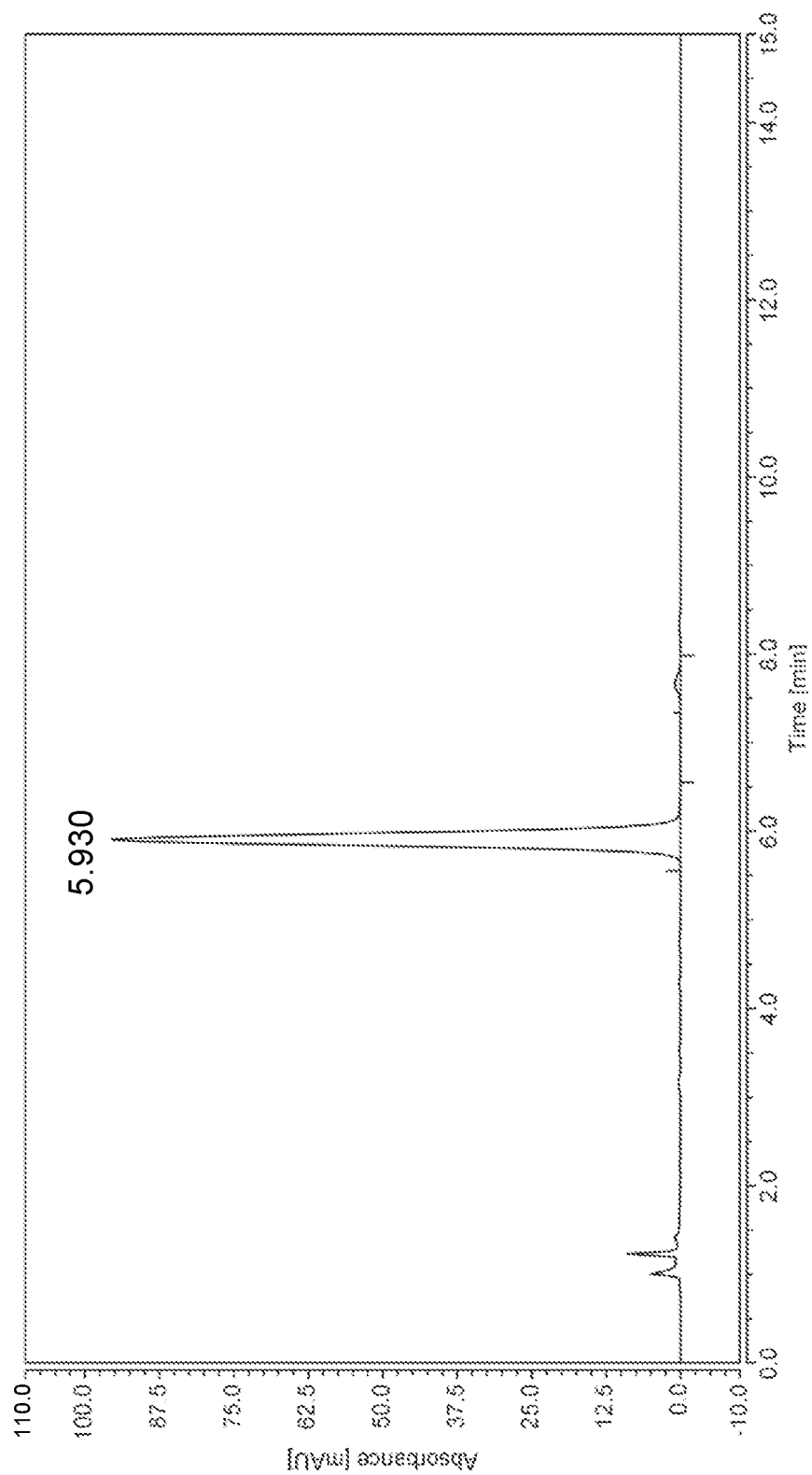
FIG. 3 illustrates a HPLC chromatogram of a reduced $CoQ_{10}$ according to some embodiments of the present disclosure.

FIG. 2 and FIG. 3 illustrate HPLC chromatograms of an oxidized $CoQ_{10}$ and reduced $CoQ_{10}$ according to some embodiments of the present disclosure, respectively.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Figure 4:
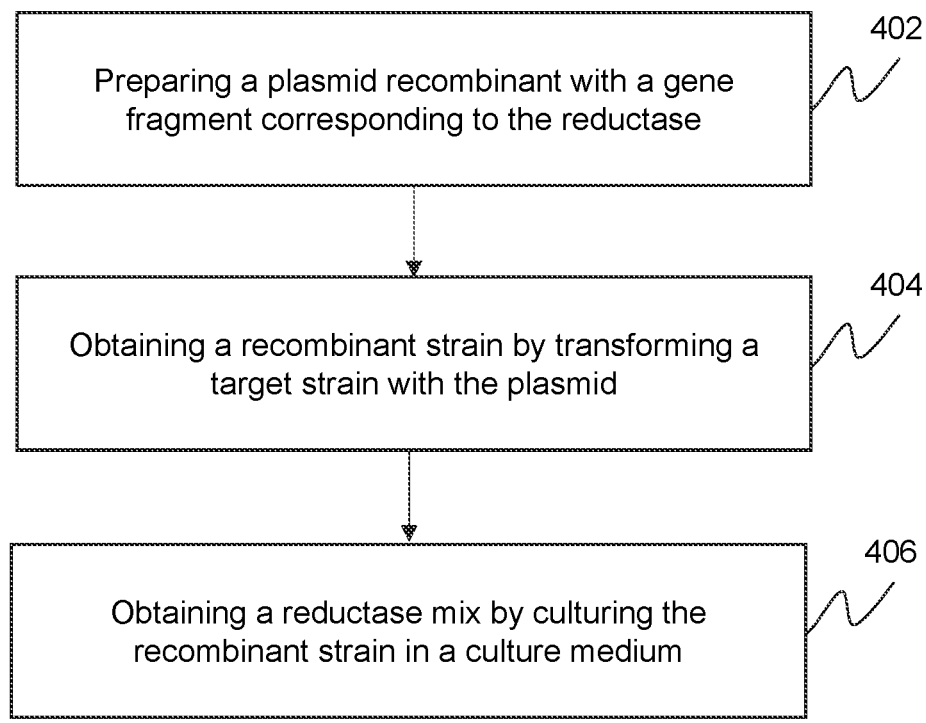
FIG. 4 is a flowchart illustrating an exemplary process for preparing reductase according to some embodiments of the present disclosure.

In some embodiments, the reductase and the coenzyme regeneration enzyme may be obtained from enzyme mixes which are prepared by fermentation processes described in FIGS. 4 and 5.

FIG. 4 is a flowchart illustrating an exemplary process for preparing a reductase according to some embodiments of the present disclosure.

In 402, a plasm id recombinant with a gene fragment corresponding to the reductase may be prepared.

The gene fragment corresponding to the reductase (e.g., LipDH, TrxR, GR) may be obtained from a genome sequence containing the gene fragment, or by DNA synthesis. In some embodiments, the gene fragment corresponding to the reductase may be codon optimized and synthesized. Codon optimization is a process used to improve gene expression and increase the translational efficiency of the reductase gene by accommodating codon bias of the host organism (e.g., E. coli). Exemplary codon optimization tool may include GenSmart™ Optimization, VectorBuilder's codon optimization tool, a codon optimization algorithm (e.g., a machine learning model), etc. The codon optimization may be performed based on an optimization strategy and some indexes. The optimization strategy is to use codons with host bias to replace less frequently occurring codons and/or adjust the original codon sequence to match the natural distribution of the host codons, the goal of which is to preserve the slow translation regions that are important for protein folding. The indexes mainly include a codon adaptation index (CAI), a frequency of relative synonymous codon usage, a codon bias index, an optimal codon usage, and an effective codon number. Among these indexes, the CAI is the primary index used to predict gene expression level because it indicates the extent to which the coding sequence represents the usage of codons in an organism. The codon-optimized gene fragment corresponding to the reductase may be digested by one or more restriction endonucleases and introduced into a plasm id to obtain a recombinant plasm id for optimal protein expression.

In some embodiments, the gene fragment corresponding to the reductase may be randomly mutated. Random mutagenesis herein is used as a powerful tool for modifying the reductase to improve a characteristic thereof (e.g., enzymatic activity), typically involving error-prone PCR (EP-PCR) or mutagenic chemicals. In some embodiments, EP-PCR may be used to generate amino acid substitutions in protein of the reductase by introducing random nucleotide mutations into the DNA sequence of the reductase during PCR. Using EP-PCR, 5' and 3' boundaries of the mutated region may be defined by the choice of PCR primers. Mutations are deliberately introduced through the use of an error prone DNA polymerases and/or reaction conditions. The DNA polymerase makes mistakes in the base paring during DNA synthesis that results in the introduction of errors in the newly synthesized complementary DNA strand of the reductase. By carefully controlling a buffer composition and a frequency of mis-incorporation of nucleotide bases, a count of errors introduced into the reductase sequence may be regulated, e.g., 1-4 amino acid changes (2-7 nucleotide changes). Types of the gene mutations of the reductase may include, for example, transition(s) (e.g., A→G, T→C, G→A, C→T), transversion(s) (e.g., A→T, T→A, A→C, T→G, G→C, C→G, G→T, C→A), insertion(s), and deletion(s).

The mutated PCR gene fragments corresponding to reductase are then cloned into the expression plasmid to obtain a resulting random mutagenesis library. In some embodiments, the needed mutations from the random mutagenesis library may be screened for changes in protein activity. By using random mutagenesis, beneficial mutations can be identified in the absence of structural information, or when such mutations are difficult to predict from protein structure.

In 404, a recombinant strain may be obtained by transforming a target strain with the plasmid.

In some embodiments, the target strain may be cultured to express the reductase. Exemplary strain may be E. coli. The plasm id recombinant with the codon optimized or mutated gene fragment corresponding to the reductase may be transformed in the target strain by electroporation or heat shock. For example, the plasm id recombinant with codon optimized and/or randomly mutated may be transformed into competent cells of the target strain (e.g., E. coli BL21) to obtain the recombinant strain.

In some embodiments, an enzymatic activity corresponding to the recombinant strain may be detected to select the beneficial mutations needed. That is, better enzymatic activity from the selected mutational strains than that from the wild type. In some embodiments, one amino acid change that results in the better reductase activity than the wild type may be selected. Merely by way of example, for LipDH, "I" at location 45 of SEQ ID NO: 1 may be changed to "S" (corresponding amino acid sequence is SEQ ID NO: 10), "R" at location 266 of SEQ ID NO: 1 may be changed to "A" (corresponding amino acid sequence is SEQ ID NO: 11), or "G" at location 272 of SEQ ID NO: 1 may be changed to "N" (corresponding amino acid sequence is SEQ ID NO: 12); for TrxR, "S" at location 91 of SEQ ID NO: 3 may be changed to "K" (corresponding amino acid sequence is SEQ ID NO: 17), or "Q" at location 193 of SEQ ID NO: 3 may be changed to "I" (corresponding amino acid sequence is SEQ ID NO: 18); for GR, "A" at location 150 of SEQ ID NO: 5 may be changed to "V" (corresponding amino acid sequence is SEQ ID NO: 20), or "P" at location 285 of SEQ ID NO: 5 may be changed to "V" (corresponding amino acid sequence is SEQ ID NO: 21). In some embodiments, the point mutations for each enzyme may be combined. For example, two or more of "I" at location 45 of SEQ ID NO: 1 changed to "S", "R" at location 266 of SEQ ID NO: 1 changed to "A", and "G" at location 272 of SEQ ID NO: 1 changed to "N" may be simultaneously present in the LipDH protein, e.g., "I" at location 45 of SEQ ID NO: 1 changed to "S" may be combined with "R" at location 266 of SEQ ID NO: 1 changed to "A" (corresponding amino acid sequence is SEQ ID NO: 13), "I" at location 45 of SEQ ID NO: 1 changed to "S" may be combined with "G" at location 272 of SEQ ID NO: 1 changed to "N (corresponding amino acid sequence is SEQ ID NO: 14), "R" at location 266 of SEQ ID NO: 1 changed to "A" may be combined with "G" at location 272 of SEQ ID NO: 1 changed to "N" (corresponding amino acid sequence is SEQ ID NO: 15), "I" at location 45 of SEQ ID NO: 1 changed to "S", "R" at location 266 of SEQ ID NO: 1 changed to "A", and "G" at location 272 of SEQ ID NO: 1 changed to "N" may be combined (corresponding amino acid sequence is SEQ ID NO: 16). As another example, "S" at location 91 of SEQ ID NO: 3 changed to "K" and "Q" at location 193 of SEQ ID NO: 3 changed to "I" (corresponding amino acid sequence is SEQ ID NO: 19) may be simultaneously present in the TrxR protein. As a further example, "A" at location 150 of SEQ ID NO: 5 changed to "V" and "P" at location 285 of SEQ ID NO: 5 changed to "V" (corresponding amino acid sequence is SEQ ID NO: 22) may be simultaneously present in the GR protein.

In some embodiments, an enzymatic activity of mutational strain may have at least 1.2 times than that of a strain without mutation. In some embodiments, the enzymatic activity of mutational strain may have 1.3, 1.5, 2.0, 4.0, 5.0, 7.0, or 9.5 times than that of a strain without mutation.

In 406, a reductase mix may be obtained by culturing the recombinant strain in a culture medium.

The recombinant strain may be cultured in a culture medium (e.g., seed culture-medium) for obtaining seed strains. After that, the seed strains may be cultured in a fermentation medium in a fermentation tank. The fermentation condition may include that a dissolved oxygen (DO) is larger than or equal to a value (e.g., 18%, 19%, 20%, 21%, 22%, etc.), air volume/culture volume/min (VVM) is 1:3, a temperate is controlled to maintain at 37° C., and pH 7.0. An inducer (e.g., IPTG) may be added to induce protein expression when OD600 reaches a preset value (e.g., 28, 29, 30, 31, 32, etc.). The inducer concentration may be 1 mM, and an inducing temperate is controlled to maintain at 25° C. After the fermentation is end, the bacteria sediment may be collected after centrifugation, a buffer solution (e.g., PBNa, or the buffer solution used in the reaction mixture to produce reduced $CoQ_{10}$) may be used to suspend the bacteria sediment and then centrifugated. The enzyme solution (i.e., the reductase mix) may be obtained, i.e., the supernate after centrifugation.

FIG. 5 is a flowchart illustrating an exemplary process for obtaining a coenzyme regeneration enzyme according to some embodiments of the present disclosure.

In 502, plasmid recombinant with a gene fragment corresponding to the coenzyme regeneration enzyme may be prepared;

In 504, a recombinant strain by transforming a target strain with the plasmid may be obtained;

In 506, a coenzyme regeneration enzyme mix by culturing the recombinant strain in a culture medium may be obtained.

The process 500 is similar to the process in FIG. 4, and the descriptions related to the overlapping details are omitted herein. The modified/mutated reductase and the coenzyme regeneration enzyme obtained by above processes have improved activity and are resistant to organic solvent (e.g., cosolvent), thereby solving the problem of poor water solubility of oxidated $CoQ_{10}$. Thus, the reductase and the coenzyme regeneration enzyme can be used in industrial production.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. For example, process 400 and 500 may be integrated into a process, that is, the reductase and the coenzyme regeneration enzyme may be prepared by a process.

The present disclosure is further described according to the following examples, which should not be construed as limiting the scope of the present disclosure.

EXAMPLES

Example 1: Acquisition of Engineering Bacteria of Reductase and Coenzyme Regeneration Enzyme The LipDH fragment (amino acid sequence shown in SEQ ID NO: 1, nucleotide sequence shown in SEQ ID NO: 7) was derived from *Oceanithermus profundus*, the TrxR fragment (amino acid sequence shown in SEQ ID NO: 2, nucleotide sequence shown in SEQ ID NO: 8) was derived from *Cereibacter sphaeroides*, the GR fragment (amino acid sequence shown in SEQ ID NO: 3, nucleotide sequence shown in SEQ ID NO: 9) was derived from *Ectothiorhodospira*, the Glucose Dehydrogenase (GDH) fragment (amino acid sequence shown in SEQ ID NO: 4) was derived from *Bacillus subtilis*, the formate dehydrogenase (FDH) fragment (amino acid sequence shown in SEQ ID NO: 5) was derived from *Candida boidinii*, and alcohol dehydrogenase fragment (amino acid sequence shown in SEQ ID NO: 6) was derived from *Bacillus*. After these fragments are codon-optimized, respectively, Changzhou Jiyu Biotechnology Co., Ltd. carried out full gene synthesis of the above fragments. Each of the fragments above after full gene synthesis was digested by restriction endonucleases Nde I and Xho I (purchased from New England Biolabs, operated according to the instructions), recombined into vector pET 28a (+) (purchased from Quanxing Gold Company), and transformed into *E. coli*. Tran5α competent cell. *E. coli* Tran5α was placed in an LB liquid medium, and shaken at 37° C., 160 rpm overnight for culturing. Recombinant plasmids LipDH-pET28a (+), Trx-pET28a (+), GR-pET28a (+) and recombinant plasmids GDH-pET28a (+), FDH-pET28a (+), ADH-pET28a (+) were extracted, respectively. The plasmids were respectively transformed into an expression host such as *Escherichia coli* BL21 (DE3) (TransGen Biotech. Co., Ltd), which is a chemically competent cell line, and recombinant *Escherichia coli* strains respectively expressing the three reductases and coenzyme regeneration enzymes were obtained.

Example 2: Preparation of Coenzyme Regeneration Enzyme

The coenzyme regeneration enzymes were prepared from the following process.

Shake Flask Fermentation

Composition of shake flask seed medium: Yeast extract: 5 g/L; Peptone: 10 g/L, NaCl: 10 g/L; Kanamycin: 50 ug/mL.

Preparation of shake flask seed medium: 5 g of yeast powder extract, 10 g of peptone, and 10 g of NaCl were dissolved in 800 mL of distilled water. The pH was adjusted to 7. The solution was diluted to 1000 mL with distilled water, and be kept at 121° C. for 15 min, and kanamycin was added to a final concentration of 50 ug/mL after cooling the solution below 60° C.

Shake flask fermentation steps included: (a) Streaking the original strains on the LB plate, culture them upside down overnight at 37° C.; (b) Picking a single clone on each plate in step (a) and inoculating it into 3 mL seed medium (a detect tube with 10 mL), culturing at 37° C. and shaking at 200 rpm for 18 hours, and stopping culture when the OD600 grows to about 1.8; (c) Inoculating 1% inoculum of strain in step (b) into 300 mL of seed medium (an Erlenmeyer flask with 1 L range), culturing at 37° C. and shaking at 200 rpm for 6 hours, and stopping culturing when the OD600 grows to about 1.5.

Fermentation Culture

The media in the fermentation culture process included a fermentation medium and a fed-batch medium.

The fermentation medium was M9 medium. The ingredients of M9 medium are as follows: 6 g/L of $Na_2HPO_4$, 3 g/L of $KH_2PO_4$, 0.246 g/L of $MgSO_4$ $7H_2O$, 2.24 g/L of $(NH_4)_2SO_4$, 0.5 g/L of NaCl, and 20 g/L of glucose.

Preparation of fermentation medium: dissolving $Na_2HPO_4$, $KH_2PO_4$, $MgSO_4$ $7H_2O$, $(NH_4)_2SO_4$, NaCl, glucose in distilled water, keeping at 121° C. for 30 min, cooling for later use. Kanamycin was sterilized by sterile membrane filtration, then added to the fermentation medium.

Composition of fed-batch medium: 600 g/L of glucose.

Preparation of fed-batch medium: dissolving of glucose in distilled water, keeping at 115° C. for 30 minutes, and cooling down for later use.

Fermentation control of fermenter: DO was controlled over 20% in the whole process, ventilation ratio was 1:3 (VVM), control temperature of fermentation culture at 37° C., and control pH at 7.0. After 8 hours of culture, dissolved oxygen was changed and the fed-batch medium was fed. IPTG was used when OD600 value was about 30. The final concentration of IPTG was 1 mM, the induction temperature was controlled at 25° C. The fermentation was stopped after culturing for 21 hours.

The bacteria ware collected by centrifugation; 50 mM of PBNa buffer was used to resuspend the bacteria, wherein the volume of PBNa buffer was 3 to 5 times the volume of bacteria. The bacteria were sonicated or homogenized, and then centrifuged to obtain the supernatants, which were the coenzyme regeneration enzyme mixes.

Example 3: Genetic Engineering on Bacteria for Producing Reductase Construction of random mutagenesis libraries for LipDH, TrxR, and GR Random mutagenesis libraries for LipDH, TrxR, and GR were constructed through error-prone PCR (EP-PCR). Specifically, with SEQ ID NO: 7 (DNA sequence of LipDH), SEQ ID NO: 8 (DNA sequence of TrxR), and SEQ ID NO: 9 (DNA sequence of GR) as templates, the random mutagenesis libraries for LipDH, TrxR, and GR were respectively constructed by using the Agilent GeneMorph II Random Mutagenesis Kit. The sequence of a forward primer (named as LipDH-Nde I-F) of LipDH is shown in SEQ ID No. 10, and the sequence of a reverse primer (named as LipDH-Xho I-R) of LipDH is shown in SEQ ID No. 11. The sequence of a forward primer (named as TrxR-Nde I-F) of TrxR is shown in SEQ ID No. 12, and the sequence of a reverse primer (named as TrxR-Nde I-R) of TrxR is shown in SEQ ID No. 13. The sequence of a forward primer (named as GR-Xho I-F) of GR is shown in SEQ ID No. 14, and the sequence of a reverse primer (named as GR-Xho I-R) of GR is shown in SEQ ID No. 15.

```
SEQ ID No. 10:
5'-GAATTCCATATGCACGATCTGATCGTAATTGGTA-3'.

SEQ ID No. 11:
5'-CCGCTCGAGTTAGCGGTTCAGGATGTGGATTGCA-3'.

SEQ ID No. 12:
5'-GAATTCCATATGCGTGGTAAAGCAATGGCAGAAA-3'.

SEQ ID No. 13:
5'-CCGCTCGAGTTATGCGCCTGCCAGAAAGCGTTCT-3'.

SEQ ID No. 14:
5'-GAATTCCATATGAACGACCATTACGATCTGATTG-3'.

SEQ ID No. 15:
5'-CCGCTCGAGTTATTTCATGGTCACCAGTTCTTCT-3'.
```

The EP-PCR system includes: 5 μL of 10× Mutazyme II reaction buffer, 1 μL of 40 mM dNTP mix (200 μM each final), 1 μL of per forward and reverse primers (10 μM), 1 μL of Mutazyme II DNA polymerase (2.5 U/μL), 50 ng plasm id template (containing SEQ ID NO: 7, SEQ ID NO: 8 or SEQ ID NO: 9), adding water to a total volume of 50 μL.

PCR procedure: 95° C. for 2 min; 95° C. for 30 s, 55° C. for 30 s, 72° C. for 1 min 30 s; 30 cycles, 72° C. for 10 min.

After amplification, gel electrophoresis was carried out. The random mutagenesis fragments were recovered from the gel, digested by restriction endonucleases Nde I and Xho I (purchased from New England Biolabs, operated according to the instructions), and recombined into vector pET 28a (+). The recombined vectors were transformed into competent cells of *E. coli.* BL21(DE3) (purchased from TransGen Biotech. Co., Ltd), thereby obtaining random mutagenesis libraries for LipDH, TrxR, and GR.

High Throughput Screening of Random Mutagenesis Libraries

LipDH transformants, TrxR transformants, and GR transformants were respectively selected from the random mutagenesis libraries by using toothpicks and inoculated in 300 μL of LB media in 96-deep well culture plates. The media contained 50 mg/L of kanamycin sulfate. The LB media were incubated overnight at 37° C. and 220 rpm. 50 μL of each primary seed liquid was transferred to 600 μL of LB medium in the secondary plate for cultivation, and incubated at 37° C. for 3 hours. For each cultivation, when OD600 is about 1.0, IPTG with a final concentration of 0.2 mM was added and the culture mix was cooled to 25° C. The bacterial cells were collected by centrifugation (3500 rpm, 10 min) after incubation overnight. 200 μL of a lysate (containing 100 mmol/L of phosphoric acid buffer, 750 mg/L of lysozyme and 12 mg/L of DNase, pH7.0) was added to each well, and the bacterial cells were shaken to make suspension uniform. Then, the suspensions were kept at 37° C. and 200 rpm/min for 2 hours. After centrifugation at 3500 rpm/min for 30 min at 4° C., supernatants of three reductases were taken into ELISA plates to detect enzyme activities. The system for measuring reductase activity in the ELISA plate includes 1 mM of oxidized $CoQ_{10}$, 20% (V/V) of cosolvent n-hexane, 0.15 mM of NADH, and PBNa buffer (0.05 M, pH7.5). The level of reductase activity was determined according to the absorption value of NADH. The mutation strains of LipDH, TrxR, and GR with high activity (represented as relative activity in Tables 1-3) were sequenced, it was found that amino acid substitutions at the mutation sites (e.g., I45S, R266A, and G272N shown in Table 1, S91K and Q193I shown in Table 2, A150V and P285V shown in Table 3) resulted in significant increases in the reductase activity of the mutation strains of LipDH, TrxR, and GR, respectively. Taking I45S as an example, I45S means that "I" at location 45 of SEQ ID NO: 1 (the amino acid sequence of LipDH) is changed to "S". Then, such amino acid substitutions of each reductase were combined. All the mutation strains as well as mutation sites and relative activities thereof were shown in Table 1-3. The original LipDH strain, original TrxR strain, and original GR strain are recombinant *Escherichia coli* strains respectively expressing the three reductases prepared in Example 1. The relative activity herein refers to a ratio of the enzymatic activity of a mutation strain to that of a wild strain.

TABLE 1

Mutation sites and relative activities of mutation strains of LipDH acid

| Strain | Mutation site | Amino acid sequence of LipDH | Relative activity |
|---|---|---|---|
| Original LipDH strain | — | SEQ ID NO: 1 | 100% |
| Mutation strain LipDH-M1 | I45S | SEQ ID NO: 10 | 150% |
| Mutation strain LipDH-M2 | R266A | SEQ ID NO: 11 | 130% |
| Mutation strain LipDH-M3 | G272N | SEQ ID NO: 12 | 120% |
| Mutation strain LipDH-M4 | I45S + R266A | SEQ ID NO: 13 | 200% |
| Mutation strain LipDH-M5 | I45S + G272N | SEQ ID NO: 14 | 225% |
| Mutation strain LipDH-M6 | R266A + G272N | SEQ ID NO: 15 | 400% |
| Mutation strain LipDH-M7 | I45S + R266A + G272N | SEQ ID NO: 16 | 950% |

TABLE 2

Mutation sites and relative activities of mutation strains of TrxR

| Strain | Mutation site | Amino acid sequence of TrxR | Relative activity |
|---|---|---|---|
| Original TrxR strain | — | SEQ ID NO: 2 | 100% |
| Mutation strain TrxR-M1 | S91K | SEQ ID NO: 17 | 150% |
| Mutation strain TrxR-M2 | Q193I | SEQ ID NO: 18 | 185% |
| Mutation strain TrxR-M3 | S91K + Q193I | SEQ ID NO: 19 | 425% |

TABLE 3

Mutation sites and relative activities of mutation strains of GR

| Strain | Mutation site | Amino acid sequence of GR | Relative activity |
|---|---|---|---|
| Original GR strain | — | SEQ ID NO: 3 | 100% |
| Mutation strain GR-M1 | A150V | SEQ ID NO: 20 | 175% |
| Mutation strain GR-M2 | P285V | SEQ ID NO: 21 | 225% |
| Mutation strain GR-M3 | A150V + P285V | SEQ ID NO: 22 | 525% |

Example 4: Determination of Reductase Activity of Original Recombinant Strains and Mutation Strains

*E. coli* BL21 (DE3) expressing LipDH-pET28a (+), TrxR-pET28a (+), GR-pET28a (+), and mutation plasm ids were inoculated into LB media containing 50 mg/L kanamycin sulfate, and incubated overnight in constant temperature shakers at 37° C. and 200 rpm. 1% of each culture medium was taken and inoculated into a fresh LB medium containing 50 mg/L kanamycin sulfate. Each medium was incubated in a constant temperature shaker at 37° C. and 200 rpm; IPTG with a final concentration of 0.1 mmol was added until OD600 is 0.8; and the media were further incubated at 25° C. for 16 hours to induce the expression of wild enzymes and mutational enzymes.

The bacterial cells of each strain were collected by centrifugation at 4° C. and 10000 rpm for 10 minutes, and resuspended in sodium phosphate buffer (50 mM, pH7.5). Cells were broken by ultrasound in an ice bath (working for 4 seconds, stopping for 4 seconds, and ultrasound for 10 minutes). Each supernatant enzyme solution was collected by centrifugation at 4° C. and 10000 rpm for 10 minutes, and purified using Ni-NTA affinity chromatography (Shanghai Shenggong Bioengineering Technology Service Co., Ltd), thereby obtaining a pure enzyme solution.

Determination procedure (1 mL): Oxidized $CoQ_{10}$ with a final concentration of 1 mmol/L (dissolved in 10 μL of n-hexane), 10 μL of NADH with a final concentration of 0.15 mmol/L, 10 μL of each pure enzyme solution, and 970 μL of PBNa buffer (0.05M, pH7.5) were mixed. The change in absorbance value at 340 nm of the mixed solution at 25° C. was detected. The unit of reductase activity (U) is defined as: the amount of reductase required to oxidize 1 μmol of NADH per minute under the above condition. The measurement results are shown in Table 4. It can be seen that compared to the original wild strain, the reductase activities of the mutation strains have significantly increased, with a relative reductase activity at most up to 950%. The above results indicate that the activities of the mutational reductases can be greatly improved by introducing mutations in wild enzymes. These mutational reductases have important practical application.

TABLE 4

Measurement results of enzyme activity

| Strain | Unit enzyme activity (U/mg) | Increase in enzyme activity |
|---|---|---|
| Original LipDH strain | 0.250 | — |
| LipDH-M1 | 0.375 | 150% |
| LipDH-M2 | 0.325 | 130% |
| LipDH-M3 | 0.300 | 120% |
| LipDH-M4 | 0.500 | 200% |
| LipDH-M5 | 0.563 | 225% |
| LipDH-M6 | 1.000 | 400% |
| LipDH-M7 | 2.375 | 950% |
| Original TrxR strain | 0.350 | — |
| TrxR-M1 | 0.525 | 150% |
| TrxR-M2 | 0.648 | 185% |
| TrxR-M3 | 1.488 | 425% |
| Original GR strain | 0.500 | — |
| GR-M1 | 0.875 | 175% |
| GR-M2 | 1.125 | 225% |
| GR-M3 | 2.625 | 525% |

Example 5: Preparation of Mutational Reductases

The fermentation of the above strains that produces mutational reductases was conducted according to the process in Example 2. After fermentation, the cells of each strain were collected by centrifugation at a speed of 5000 g for 3 minutes. The bacterial cells were suspended in a 3-fold volume of 50 mmol PBNa buffer (pH7.5), and then bacterial cells were lysed using ultrasound. The supernatant of each strain was collected after centrifugation (4° C., 10000 g, 10 min), thus obtaining each mutational enzyme mix (i.e., enzyme solution).

The obtained mutational reductase mixes obtained in Example 5 and the coenzyme regeneration enzyme mixes obtained in Example 2 were used in the following examples.

Example 6: Comparison of Enzyme-Catalyzed Reactions Between Different Reductases 5 ml of PBNa buffer (0.05M, pH7.0), 0.25 g of glucose, 0.2 mg of NADP+, and 0.4 g of oxidized $CoQ_{10}$ were mixed.

Three groups of mixed solutions containing the above ingredients was repeatedly. 0.1 g of LipDH, TrxR, GR, and 0.05 g of GDH mix were added to each group to react at 37° C. and 200 rpm, and samples were taken regularly during the reaction. Table 5 lists the detection results of the purity of CoQH (reduced $CoQ_{10}$) produced by the three reductases at different enzymatic reaction times. The purity of CoQH is determined according to the formula (1).

The results in Table 5 show that the CoQH produced by the reductase LipDH has the highest purity. When the enzymatic reaction time reaches 24 h, the purity of CoQH is as high as 96.6%.

TABLE 5

Purity of CoQH produced by three reductases at different enzymatic reaction times

| Reductase | Purity of CoQH | | | | | | |
|---|---|---|---|---|---|---|---|
| | 2 h | 4 h | 8 h | 12 h | 16 h | 20 h | 24 h |
| LipDH | 48.9 | 69.1 | 87.2 | 90.4 | 93.8 | 96.2 | 96.6 |
| TrxR | 42.2 | 57.3 | 86.5 | 89.7 | 93.5 | 95.2 | 96.2 |
| GR | 45.2 | 67.4 | 84.5 | 89.2 | 92.5 | 95.3 | 95.7 |

Example 7: Comparision of Different Cosolvents 0.4 g of oxidated $CoQ_{10}$ was dissolved in 1 ml of DMSO, toluene, ethyl acetate, n-hexane, THF, MTBE, ethanol, and n-heptane respectively to obtain 8 groups of oxidated $CoQ_{10}$ solutions. 5 ml of PBNa buffer (0.05M, pH7.0), 0.25 g of glucose, 0.2 mg of $NADP^+$ were added to each group of oxidated $CoQ_{10}$ solutions, mixed well, then 0.1 g of LipDH mix and 0.05 g of GDH mix was added to each group of solutions, reacted at 37° C. and 200 rpm. Samples were taken regularly during the reaction for detecting. Table 2 lists the detection results of the purity of CoQH produced by dissolving $CoQ_{10}$ in different cosolvents. The results in Table 2 show that when n-hexane, n-heptane or MTBE is used as the cosolvent of oxidated $CoQ_{10}$, the purity of the produced CoQH is the highest.

TABLE 6

Purity of CoQH produced by $CoQ_{10}$ dissolved in different cosolvents

| Cosolvent | Purity of CoQH | | | | | | |
|---|---|---|---|---|---|---|---|
| | 2 h | 4 h | 8 h | 12 h | 16 h | 20 h | 24 h |
| DMSO | 67.2 | 75.4 | 85.5 | 92.2 | 95.1 | 98.2 | 97.8 |
| toluene | 55.6 | 67.1 | 75.2 | 82.9 | 90.5 | 94.2 | 96.1 |
| ethyl acetate | 1.8 | 3.5 | 5.5 | 8.2 | 8.8 | 9.0 | 9.8 |
| n-hexane | 71.1 | 83.5 | 89.2 | 94.5 | 98.2 | 99.2 | 99.0 |
| THF | 2.5 | 5.8 | 10.2 | 15.3 | 17.8 | 17.5 | 17.2 |
| MTBE | 68.5 | 77.2 | 88.9 | 93.7 | 97.2 | 99.0 | 99.2 |
| ethanol | 55.2 | 68.4 | 75.5 | 82.2 | 88.3 | 91.1 | 93.3 |
| n-heptane | 70.2 | 82.8 | 90.5 | 95.0 | 97.7 | 98.6 | 99.2 |

Example 8: Influence of Metal Ion 0.4 g of oxidated $CoQ_{10}$ was dissolved in 1 ml of n-hexane, 5 ml of PBNa buffer (0.05M, pH7.0), 0.25 g of glucose, and 0.2 mg of $NADP^+$ were mixed. Six groups of mixed solutions containing the above ingredients were repeated. 20 mM of metal ions solution ($MgCl_2$, $ZnCl_2$, $MnCl_2$, $CoCl_2$, $FeCl_2$, $CaCl_2$, respectively) were added to each group of mixed solutions, mixed well, 0.1 g of LipDH reductase and 0.05 g of GDH enzyme solution was added, reacted at 37° C., 200 rpm. Samples were taken during the reaction periodically for detection. Table 7 lists the detection results of the purity of CoQH produced by the reaction system under the addition of different metal ions. The detection results in Table 7 show that further adding metal ions to the reaction mixture can improve the purity of the produced CoQH. Among them, when using $Zn^{2+}$ or $Cd^{2+}$ as metal ions to participate in the enzymatic reaction, the purity of the produced CoQH is the highest. When the enzymatic reaction time was 24 h, the purity of CoQH was as high as 99.6%. The added metal ions can increase the reaction speed and short the reaction time compared to the reaction process without metal ions.

TABLE 7

The influence of different metal ions on the purity of CoQH

| Metal ion | Purity of CoQH | | | | | | |
|---|---|---|---|---|---|---|---|
| | 2 h | 4 h | 8 h | 12 h | 16 h | 20 h | 24 h |
| $MgCl_2$ | 72.1 | 82.3 | 89.1 | 93.9 | 98.7 | 99.4 | 98.9 |
| $ZnCl_2$ | 87.5 | 98.2 | 99.4 | 99.2 | 99.3 | 99.6 | 99.5 |
| $MnCl_2$ | 70.4 | 81.2 | 88.0 | 92.7 | 98.1 | 99.2 | 99.3 |
| $CoCl_2$ | 71.6 | 82.0 | 90.3 | 94.5 | 98.7 | 99.4 | 99.5 |
| $CdCl_2$ | 86.8 | 98.6 | 99.2 | 99.3 | 99.7 | 99.6 | 99.6 |
| $CaCl_2$ | 71.9 | 84.6 | 89.4 | 93.1 | 97.8 | 98.9 | 99.2 |

Example 9: Influence of Reductase Level 5 ml of PBNa buffer (0.05M, pH7.0), 0.25 g of glucose, 0.2 mg of $NADP^+$, 20 mM of $ZnCl_2$, 0.4 g of oxidated $CoQ_{10}$ (added after dissolving in 1 ml of n-hexane) were mixed. 6 groups of mixed solutions containing the above ingredients were repeatedly prepared, different levels of LipDH mix (0.01 g, 0.02 g, 0.05 g, 0.1 g, 0.15 g, 0.2 g) and 0.05 g of GDH mix were added to each group of mixed solutions, reacted at 37° C. and 200 rpm, and samples were taken regularly during the reaction for detecting. Table 8 lists the results of the purity of CoQH produced under different levels of reductase. The results in Table 8 show that when the level of reductase is between 0.01-0.1 g, the purity of CoQH produced gradually increases with the increase of the level of reductase. When the level of reductase is greater than 0.1 g, the purity of CoQH produced no longer increases with the increase of the level of reductase. Therefore, using 0.1 g of reductase to participate in the reaction can save production costs while ensuring the purity of CoQH.

TABLE 8

The impact of the different levels of reductase on the purity of CoQH

| Level of reductase (g) | Purity of CoQH | | | | | | |
|---|---|---|---|---|---|---|---|
| | 2 h | 4 h | 8 h | 12 h | 16 h | 20 h | 24 h |
| 0.01 | 48.2 | 53.5 | 56.2 | 57.4 | 59.0 | 58.6 | 59.1 |
| 0.02 | 55.7 | 70.2 | 89.4 | 95.3 | 97.9 | 98.2 | 99.0 |
| 0.05 | 68.5 | 88.2 | 96.1 | 98.4 | 99.0 | 99.4 | 99.4 |
| 0.10 | 86.7 | 98.3 | 99.4 | 99.3 | 99.5 | 99.5 | 99.6 |
| 0.15 | 87.9 | 98.9 | 99.3 | 99.5 | 99.4 | 99.4 | 99.5 |
| 0.20 | 90.4 | 99.2 | 99.5 | 99.6 | 99.6 | 99.5 | 99.6 |

Example 10: Influence of Different pH Values 5 ml of PBNa buffer solution (0.05M) with pH values of 4.0, 5.0, 6.0, 7.0, 8.0, and 9.0 were prepared respectively, and 0.25 g of glucose, 0.2 mg of $NADP^+$, 20 mM of $ZnCl_2$, 0.4 g of oxidated $CoQ_{10}$ (dissolved in 1 ml of n-hexane) were added, mixed well. 0.1 g of LipDH reductase and 0.05 g of GDH mix were added to each group of solutions, reacted at 37° C. and 200 rpm, and samples were taken regularly during the reaction. Table 9 lists the results of the purity of CoQH produced at different pH values. The results in Table 9 show that when the pH is between 6-8, the purity of the produced CoQH is higher.

TABLE 9

The influence of different pH on the purity of CoQH

| pH value | Purity of CoQH | | | | | | |
|---|---|---|---|---|---|---|---|
| | 2 h | 4 h | 8 h | 12 h | 16 h | 20 h | 24 h |
| 4 | 15.1 | 22.4 | 27.2 | 31.5 | 34.1 | 36.2 | 37.3 |
| 5 | 39.6 | 57.8 | 74.6 | 86.9 | 92.0 | 94.6 | 97.3 |
| 6 | 77.8 | 93.4 | 97.8 | 98.6 | 99.1 | 99.3 | 99.4 |
| 7 | 84.6 | 96.2 | 99.0 | 99.5 | 99.7 | 99.5 | 99.5 |
| 8 | 86.5 | 92.9 | 98.5 | 99.4 | 99.4 | 99.5 | 99.6 |
| 9 | 38.1 | 45.2 | 50.5 | 52.7 | 55.6 | 57.5 | 58.1 |

Example 11: Influence of Different Reaction Temperatures 5 ml of PBNa buffer (0.05M, pH 7.0), 0.25 g of glucose, 0.2 mg of $NADP^+$, 20 mM of $ZnCl_2$, 0.4 g of oxidated $CoQ_{10}$ (dissolved in 1 ml of n-hexane) were mixed. 0.1 g of LipDH mix and 0.05 g of GDH mix were added to the mixed solution. 8 groups of mixed solutions containing the above ingredients were repeatedly prepared, reacted at 20° C., 25° C., 30° C., 35° C., 37° C., 40° C., 45° C., and 50° C., respectively (kept rotating speed 200 rpm), and samples were taken regularly during the reaction. Table 10 lists the results of the purity of CoQH produced at different temperatures. The results in Table 10 shows that when the temperature is in a range of 25-40° C., the purity of the produced CoQH is relatively high.

TABLE 10

The influence of different temperatures on the purity of CoQH

| Temperature | Purity of CoQH | | | | | | |
|---|---|---|---|---|---|---|---|
| | 2 h | 4 h | 8 h | 12 h | 16 h | 20 h | 24 h |
| 20° C. | 20.2 | 35.7 | 47.3 | 54.5 | 59.1 | 64.2 | 67.5 |
| 25° C. | 48.1 | 69.8 | 83.3 | 97.2 | 98.4 | 98.6 | 99.0 |
| 30° C. | 82.9 | 97.2 | 98.8 | 98.9 | 99.2 | 99.2 | 99.1 |
| 35° C. | 90.0 | 96.9 | 99.1 | 99.4 | 99.5 | 99.4 | 99.4 |
| 37° C. | 91.2 | 97.8 | 99.1 | 99.3 | 99.5 | 99.4 | 99.5 |
| 40° C. | 96.7 | 98.2 | 99.2 | 99.2 | 99.4 | 99.5 | 99.4 |
| 45° C. | 59.8 | 66.5 | 72.7 | 77.2 | 82.3 | 81.9 | 82.1 |
| 50° C. | 11.2 | 18.5 | 22.8 | 25.2 | 28.5 | 29.8 | 30.7 |

Example 12

500 ml of PBNa buffer (0.05M, pH7.0), 25 g of glucose, 20 mg of $NADP^+$, 20 mM of $ZnCl_2$, and 40 g of oxidated $CoQ_{10}$ (dissolved in 100 ml of n-hexane) were mixed. 10 g of LipDH mix and 5 g of GDH mix were added to the mixed solution to react at 37° C. and 200 rpm for 4 hours. The reacted solution was stood for phase separation, the oil layer was washed with 50 ml of pure water for 3 times and was concentrated to dryness under reduced pressure at 45° C. 400 ml of 95% ethanol was added to the dried oil layer, and the obtained solution was crystallized for more than 3 hours under a temperature of 10-25° C., and was filtered to obtain the crystalline product. The crystalline product was vacuum-dried at 40° C. to obtain 36.9 g of reduced $CoQ_{10}$ with a purity of 99.0%.

Example 13

500 ml of PBNa buffer (0.05M, pH7.0), 25 g of glucose, 20 mg of $NAD^+$, 20 mM of ZnCl2, and 40 g of oxidated $CoQ_{10}$ (dissolved in 100 ml of n-hexane) was mixed. 10 g of LipDH mix, 5 g of GDH mix were added to the mixed solution to react at 37° C. and 200 rpm for 4 hours. The reacted solution was stood for phase separation, the oil layer was washed with 50 ml of pure water for 3 times and was concentrated to dryness under reduced pressure at 45° C., 400 ml of 95% ethanol was added to the dried oil layer, and the obtained solution was crystallized for more than 3 hours under a temperature of 10-25° C., and was filtered to obtain the crystalline product. The crystalline product was vacuum-dried at 40° C. to obtain 37.1 g of CoQH with a purity of 99.2%.

Example 14

500 ml of Tris-HCl buffer (0.05M, pH6.5), 50 g of glucose, 40 mg of $NADP^+$, 20 mM of $ZnCl_2$, and 80 g of oxidated $CoQ_{10}$ (dissolved in 200 ml of n-hexane) were mixed. 10 g of LipDH mix and 5 g of GDH mix were added to the mixed solution to react at 37° C. and 200 rpm for 8 hours. The reacted solution was stood for phase separation, the oil layer was washed with 50 ml of pure water for 3 times and was concentrated to dryness under reduced pressure at 45° C. 800 ml of 95% ethanol was added to the dried oil layer, and the obtained solution was crystallized for more than 3 hours under a temperature of 10-25° C. The crystalline product was obtained by filtration. And then the crystalline product was further vacuum-dried at 40° C. to obtain 75.2 g of the reduced $CoQ_{10}$ with a purity of 99.1%.

Example 15

500 ml of Tris-HCl buffer (0.05M, pH7.0), 25 g of glucose, 20 mg of $NADP^+$, 20 mM of $ZnCl_2$, and 40 g of oxidated $CoQ_{10}$ (dissolved in 80 ml of n-hexane) were mixed. 10 g of GR mix and 5 g of GDH mix were added to the mixed solution to react at 37° C. and 200 rpm for 4 hours. The reacted solution was stood for phase separation, the oil layer was washed with 50 ml of pure water for 3 times and the washed oil layer was concentrated to dryness under reduced pressure at 45° C. 800 ml of 95% ethanol was added to the dried oil layer, and the obtained solution was crystallized for more than 3 hours under a temperature of 10-25° C. And thus, the crystalline product was obtained by filtration. The crystalline product was further vacuum-dried at 40° C. to obtain 37.6 g of the CoQH with a purity of 99.4%.

Example 16

500 ml of Tris-HCl buffer (0.05M, pH7.5), 25 g of glucose, 20 mg of $NADP^+$, 20 mM of $ZnCl_2$, and 40 g of oxidated $CoQ_{10}$ (dissolved in 100 ml of n-hexane and added) were mixed. 10 g TrxR mix and 5 g of GDH mix were added to the mixed solution to react at 37° C. and 200 rpm for 6 hours. The reacted solution was stood for phase separation, the oil layer was washed with 50 ml of pure water for 3 times and the washed oil layer was concentrated to dryness under reduced pressure at 45° C. 800 ml of 95% ethanol was added to the concentrated oil layer, and the obtained solution was dried for more than 3 hours under a temperature of 10-25° C. And thus, the crystalline product was obtained by filtration. The crystalline product was further vacuum-dried at 40° C. to obtain 38.2 g of the CoQH with a purity of 98.8%.

Example 17

500 ml of Tris-HCl buffer (0.05M, pH6.5), 25 g of glucose, 20 mg of $NADP^+$, 20 mM of $ZnCl_2$, and 40 g of oxidated $CoQ_{10}$ (dissolved in 100 ml of n-hexane) were mixed. 10 g TrxR mix and 5 g of GDH mix were added to the mixed solution to react at 40° C. and 200 rpm for 4 hours. The reacted solution was stood for phase separation, the oil layer was washed with 50 ml of pure water for 3 times and the washed oil layer was concentrated to dryness under reduced pressure at 45° C. 800 ml of 95% ethanol was added to the dried oil layer, and the obtained solution was crystallized for more than 3 hours under a temperature of 10-25° C. And thus, the crystalline product was obtained by filtration. The crystalline product was further vacuum-dried at 40° C. to obtain 37.6 g of the CoQH with a purity of 98.8%.

Example 18

500 ml of Tris-HCl buffer (0.05M, pH6.5), 25 g of glucose, 20 mg of $NADP^+$, 20 mM of $ZnCl_2$, and 40 g of oxidated $CoQ_{10}$ (dissolved in 50 ml DMSO) were mixed. 10 g of TrxR mix and 5 g of GDH mix were added to the mixed solution to react at 40° C. and 200 rpm for 6 hours, 200 ml of n-hexane for extraction were added. The reacted solution was stood for phase separation, the oil layer was washed with 50 ml of pure water for 3 times and the washed oil layer was concentrated to dryness under reduced pressure at 45° C. 800 ml of 95% ethanol was added to the dried oil layer, and the obtained solution was crystallized for more than 3 hours under a temperature of 10-25° C., and thus the crystalline product was obtained by filtration. The crystalline product was further vacuum-dried at 40° C. to obtain 37.6 g of CoQH with a purity of 98.8%.

Example 19

500 ml of Tris-HCl buffer (0.05M, pH6.5), 25 g of glucose, 20 mg of $NADP^+$, 20 mM of $ZnCl_2$, and 40 g of oxidated $CoQ_{10}$ (dissolved in 100 ml MTBE) were mixed. 10 g of GR mix and 5 g of GDH mix were added to the mixed solution to react at 35° C. and 200 rpm for 6 hours. The reacted solution was stood for phase separation, the oil layer was washed with 50 ml of pure water for 3 times and the washed oil layer was concentrated to dryness under reduced pressure at 45° C. 800 ml of 95% ethanol was added to the dried oil layer, and the obtained solution was crystallized for more than 3 hours under a temperature of 10-25° C., and thus the crystalline product was obtained by filtration. The crystalline product was further vacuum-dried at 40° C. to obtain 37.9 g of CoQH with a purity of 99.3%.

Example 20

500 ml of PBNa buffer (0.05M, pH6.5), 10 g ammonium formate, 20 mg of $NAD^+$, 20 mM of $ZnCl_2$, and 40 g of oxidated $CoQ_{10}$ (dissolved in 100 ml of n-hexane) were mixed. 15 g of GR reductase and 7.5 g of FDH mix were added to the mixed solution to react at 35° C. and 200 rpm for 4 hours. The reacted solution was stood for phase separation, the oil layer was washed with 50 ml of pure water for 3 times and the washed oil layer was concentrated under reduced pressure at 45° C. 800 ml of 95% ethanol was added to the concentrated oil layer, and the obtained solution was crystallized for more than 3 hours under a temperature of 10-25° C. And thus, the crystalline product was obtained by filtration. The crystalline product was further vacuum-dried at 40° C. to obtain 38.0 g of the CoQH with a purity of 99.0%.

Example 21

500 ml of Tris-HCl buffer (0.05M, pH7.0), 15 g ammonium formate, 20 mg of $NAD^+$, 20 mM of $ZnCl_2$, and 60 g of oxidated $CoQ_{10}$ (dissolved in 100 ml of n-hexane) were mixed. 15 g of TrxR reductase and 7.5 g of FDH mix were added to the mixed solution to react at 35° C. and 200 rpm for 4 hours. The reacted solution was stood for phase separation, the oil layer was washed with 50 ml of pure water for 3 times and the washed oil layer was concentrated to dryness under reduced pressure at 45° C. 800 ml of 95% ethanol was added to the dried oil layer, and the obtained solution was crystallized for 3 hours under a temperature of 10-25° C. And thus, the crystalline product was obtained by filtration. The crystalline product was further vacuum-dried at 40° C. to obtain 56.5 g of the CoQH with a purity of 99.1%.

Example 22

500 ml of Tris-HCl buffer (0.1M, pH7.0), 15 g ammonium formate, 20 mg of $NAD^+$, 20 mM of $ZnCl_2$, and 60 g of oxidated $CoQ_{10}$ (dissolved in 200 ml of n-hexane) were mixed. 15 g of LipDH reductase and 7.5 g of FDH mix were added to the mixed solution to react at 35° C. and 200 rpm for 4 hours. The reacted solution was stood for phase separation, the oil layer was washed with 50 ml of pure water for 3 times and the washed oil layer was concentrated to dryness under reduced pressure at 45° C. 800 ml of 95% ethanol was added to the concentrated oil layer, and the obtained solution was crystallized for 3 hours under a temperature of 10-25° C. And thus, the crystalline product was obtained by filtration. The crystalline product was further vacuum-dried at 40° C. to obtain 56.9 g of CoQH with a purity of 99.3%.

Example 23

500 ml of Tris-HCl buffer (0.05M, pH7.0), 16.7 g of isopropanol, 20 mg of $NAD^+$, 20 mM of $ZnCl_2$, and 60 g of oxidated $CoQ_{10}$ (dissolved in 100 ml of n-hexane) were mixed. 15 g of LipDH reductase and 7.5 g of ADH mix were added to the mixed solution to react at 35° C. and 200 rpm for 4 hours. The reacted solution was stood for phase separation, the oil layer was washed with 50 ml of pure water for 3 times, and the washed oil layer was concentrated to dryness under reduced pressure at 45° C. 800 ml of 95% ethanol was added to the dried oil layer, and the obtained solution was crystallized for more than 3 hours under a temperature of 10-25° C., and thus a crystalline product was obtained by filtration. The crystalline product was further vacuum-dried at 40° C. to obtain 57.8 g of CoQH with a purity of 99.2%.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer-readable medium having computer readable program code embodied thereon.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A process for producing reduced coenzyme $Q_{10}$ ($CoQ_{10}$), comprising:

preparing a reaction mixture, which includes oxidized $CoQ_{10}$, a reductase, a supplement coenzyme, a coenzyme regeneration enzyme, and a substrate of the coenzyme regeneration enzyme, wherein the reductase comprises glutathione reductase (GR) derived from *Ectothiorhodospira haloalkaliphil*, and has the amino acid sequence of SEQ ID NO: 3, and the coenzyme regeneration enzyme comprises glucose dehydrogenase (GDH) derived from *Bacillus subtilis*, and has the amino acid sequence of SEQ ID NO: 4; and providing a condition so that components of the reaction mixture react to produce the reduced $CoQ_{10}$.

2. The process of claim 1, wherein the supplement coenzyme is $NAD^+$ or $NADP^+$.

3. The process of claim 1, wherein the reaction mixture is a solution that includes a cosolvent, a metal ion, and a buffer solution, wherein the cosolvent includes at least one of MTBE, n-hexane, n-heptane, toluene, dimethylsulfoxide (DMSO), and ethanol; the metal ion includes $Zn^{2+}$ or $Cd^{2+}$; and the buffer solution includes a Tris-HCl buffer solution, a phosphate buffer solution, triethanolamine hydrochloride, sodium acetate buffer solution, or Tris-phosphate buffer solution.

4. The process of claim 1, wherein the mass concentration of the oxidized $CoQ_{10}$ in the reaction mixture is at 1%-30%, and the mass concentration is a ratio of the mass of the oxidized $CoQ_{10}$ to a volume of the reaction mixture in a form of grams/100 ml.

5. The process of claim 4, wherein the weight ratio of the reductase to the oxidized $CoQ_{10}$ is in a range of 0.01-1.

6. The process of claim 1, wherein the coenzyme regeneration enzyme is the GDH, the substrate is glucose, and the weight ratio of the GDH to the oxidized $CoQ_{10}$ is in a range of 0.05-0.25.

7. The process of claim 6, wherein the molar ratio of the glucose to the oxidized $CoQ_{10}$ is in a range of 2-6.

8. The process of claim 4, wherein the weight ratio of the supplement coenzyme to the oxidized $CoQ_{10}$ is in a range of $10^{-4}$-$10^{-3}$, wherein the supplement coenzyme is $NAD^+$ or $NADP^+$.

9. The process of claim 1, wherein the condition includes the pH of the reaction mixture is maintained in a range of 5.0-8.0; the temperature of the reaction mixture is maintained at 25-40° C.; or a reaction time is in a range of 2-24 h.

10. The process of claim 1, wherein the reductase or the coenzyme regeneration enzyme is prepared by a process including:

preparing a recombinant plasmid with a gene fragment corresponding to the reductase or the coenzyme regeneration enzyme;

obtaining a recombinant strain by transforming a target strain with the recombinant plasmid with the gene fragment corresponding to the reductase or the coenzyme regeneration enzyme; and obtaining a reductase mix or a coenzyme regeneration enzyme mix by culturing the recombinant strain in a culture medium.

11. The process of claim 10, wherein the gene fragment corresponding to the reductase or the coenzyme regeneration enzyme is codon optimized.

* * * * *

```
                            SEQUENCE LISTING

Sequence total quantity: 22
SEQ ID NO: 1             moltype = AA  length = 461
FEATURE                  Location/Qualifiers
source                   1..461
                         mol_type = protein
                         organism = Oceanithermus profundus
SEQUENCE: 1
MYDLIVIGTG PGGYHAAIRA AQLGLKVAAV EAGAVGGVCL NVGCIPTKAL LHAAETLEHA    60
AKGAEFGLVF SEAERDLAKM GRWRDKIVKK LTGGVASLLK GNGVELVKGF ARFTGPRELE   120
VDGKKLEAKK IIVATGSKPA VLPGFEPDGE HVLTSTEMLR VENGVPARLL VIGGGVIGLE   180
FASIYARLGA EVTVVEYEGQ ILPGSDPELV KLLARSLKKQ GIVVKTATKA AGYEKAGGGL   240
RVTVEPAAGG EQEVLDADKI LLAVGRVPFT EGLNLEAAGV RTDERGFVPT NEHLETNVPG   300
VYAIGDVTKP PLLAHKAMKE GLVAAEHAAG RPAAFDQQIP SVVYTQPEFA SVGMTEAEAK   360
ARGLEVRVGR FPFSASGRAL TLQQTEGLIK LVADAENDLL LGAHILGPGA SDLIAEATLA   420
LEMAATAGDL ALTVHPHPTL AENLMEAAEN LHGRAIHILN R                      461

SEQ ID NO: 2             moltype = AA  length = 317
FEATURE                  Location/Qualifiers
source                   1..317
                         mol_type = protein
                         organism = Cereibacter sphaeroides
SEQUENCE: 2
MRGKAMAETR HTRVLIIGSG PAGYTAAVYS ARAMLNPLLI QGLQPGGQLT ITTEVENWPG    60
DREVQGPELM VRMEDHARAM GAEIVSDYIS SLDLSQRPFT ARADSGMTYT ADAVILATGA   120
QARWLGLPSE ERFKGFGVSA CATCDGFFYR GKEVVVAGGG NTAVEEALFL TNFASKVTLV   180
HRRDSLRAEK ILQDRLFKHP KIEVLWNHTI EEVAGTEAPL GVTGIVARNV LTGETTEVPC   240
EGFFVAIGHA PASELVKDQL ELHHGGYVRV EPGTTRTSIP GVFAAGDLTD HVYRQAVTSA   300
GMGCMAALDA ERFLAGA                                                 317

SEQ ID NO: 3             moltype = AA  length = 448
FEATURE                  Location/Qualifiers
source                   1..448
                         mol_type = protein
                         organism = Ectothiorhodospira shaposhnikovii
SEQUENCE: 3
MNDHYDLIAI GAGSGGLSVV ERAARYGALC AVVESGPLGG TCVNVGCVPK KVMWYAADMA    60
```

```
HRLDDAPGYG FKLAREGFDW SELVGARDAY IEGINTWYHT YLADSGVDEI PGRARFVDAH    120
TLEVDGRRVS ADHVVIAVGG QPSVPDIPGA ELGITSDGFF QLKSQPRRVA VIGAGYIAVE    180
LAGMLRALGS EVSMYLRRQT LLRSFDPMLR DTLMEQMLAD GVNLFPSTQV GRLIAHPDSV    240
ELFCDQGECR GVFDQVIWAT GRTPATNDLD LHNTGIQPDD QGYIPTDLYQ NTSVEGVYAI    300
GDVTGRAPLT PVAIAAGRRL ADRLFGGQTD RHLSYETIPS VIFSHPPIGT VGLTEEEARA    360
AHGEAVKVYS TRFTSMYHAM TPHKVATAMK LVTVGAQEKV VGVHIIGPDA DEMLQGFAVA    420
VRMGATKRDL DDTVALHPTS AEELVTMK                                      448

SEQ ID NO: 4              moltype = AA   length = 261
FEATURE                   Location/Qualifiers
source                    1..261
                          mol_type = protein
                          organism = Bacillus subtilis
SEQUENCE: 4
MYPDLKGKVV AITGAASGLG KAMAIRFGKE QAKVVINYYS NKQDPNEVKE EVIKAGGEAV     60
VVQGDVTKEE DVKNIVQTAI KEFGTLDIMI NNAGLENPVP SHEMPLKDWD KVIGTNLTGA    120
FLGSREAIKY PVENDIKGNV INMSSVHEVI PWPLFVHYAA SKGGIKLMTE TLALEYAPKG    180
IRVNNIGPGA INTPINAEKF ADPKQKADVE SMIPMGYIGE PEEIAAVAAW LASKEASYVT    240
GITLFADGGM TKYPSFQAGR G                                             261

SEQ ID NO: 5              moltype = AA   length = 364
FEATURE                   Location/Qualifiers
source                    1..364
                          mol_type = protein
                          organism = Candida boidinii
SEQUENCE: 5
MKIVLVLYDA GKHAADEEKL YGCTENKLGI ANWLKDQGHE LITTSDKEGE TSELDKHIPD     60
ADIIITTPFH PAYITKERLD KAKNLKLVVV AGVGSDHIDL DYINQTGKKI SVLEVTGSNV    120
VSVAEHVVMT MLVLVRNFVP AHEQIINHDW EVAAAIAKDAY DIEGKTIATI GAGRIGYRVL   180
ERLLPFNPKE LLYYDYQALP KEAEEKVGAR RVENIECELV QADIVTVNAP LHAGTKGLIN    240
KELLSKFKKG AWLVNTARGA ICVAEDVAAA LESGQLRGYG GDVWFPQPAP KDHPWRDMRN    300
KYGAGNAMTP HYSGTTLDAQ TRYAEGTKNI LESFFTGKFD YRPQDIILLN GEYVTKAYGK    360
HDKK                                                                364

SEQ ID NO: 6              moltype = AA   length = 338
FEATURE                   Location/Qualifiers
source                    1..338
                          mol_type = protein
                          organism = Bacillus pseudomycoides
SEQUENCE: 6
MKAAVVNEFK EKLEVKEVPK PKAELGEVLV HIEACGVCHT DLHAAHGDWP VKPKLPLIPG     60
HEGVGVIEEV GEGVTHVKVG DRVGVPWLYS ACGHCEYCLS GRETLCLDQH NAGYSVDGGY    120
AEYCVAAADY VVKVPDNLEF VDAAPLFCAG VTTYKALKVS EAKPGDWVAI FGIGGLGHLA    180
VQYAKAMGLH VVAVDTVDDK LELAKELGAD LAVNPLKEDA AAWIFEKVKG VHASICTAVS    240
KPAFDQAYRS VRRGGACVAV GLPPEMMEVP IFDTVLNGVK IIGSIVGTRK DLQETLQFAA    300
EGKVKAIIET RHLDEINEIF SEMEEGKING RVVLDMTK                           338

SEQ ID NO: 7              moltype = DNA   length = 1383
FEATURE                   Location/Qualifiers
source                    1..1383
                          mol_type = genomic DNA
                          organism = Oceanithermus profundus
SEQUENCE: 7
atgtacgacc tgattgtgat tggcaccggt ccgggcggtt atcatgcagc aattcgcgcc     60
gccgctggg gtttaaaagt tgccgcagtg gaagcaggta cagttggtgg tgtgtgcctg    120
aatgtgggtt gcattccgac caaagcactg ctgcatcagg ccgaaaccct ggaacatgcc    180
gccaaaggcg cagaatttgg cctggttttt agcgaagcag aacgtgatct ggccaaaatg    240
ggtcgctggc gcgataaaat tgtgaaaaaa ctgaccggtg cgttgccag tctgctgaaa    300
ggtaatggtg tggaactggt taaaggcttt gcacgtttta ccgccccgcg tgaactggaa    360
gttgatggta aaaaactgga agcaaagaag atcatcgtgg caaccggtag taaccggca    420
gttctgccgg gctttgaacc ggatggcgaa catgtgctga ccagcaccga aatgctgcgc    480
gtggaaaatg gcgttccggc cagactgctg gttattggtg gcggtgttat tggtctggaa    540
tttgccagca tctatgcacg cctgggtgca gaagtgaccg ttgtgaata tgaaggccag    600
attctgccgg gtagtgatcc ggaactggtt aagctgcctg ccgtagcct gaaaaaccag    660
ggtattgtgg tgaaaaccgc caccaaagca gccggttatg aaaaagcagg tggtggcctg    720
cgtgtgaccg tggagcctgc cgctggtggt gagcaggagg tgttagatgc agataaaatt    780
ctgctggccg ttggccgcgt gccgtttacc gagggtttaa atctggaagc cgcaggtgtt    840
cgcaccgatg aactgtggtt tgttccgacc aatgaacatc tggaaaccaa tgtgccggt    900
gtgtatgcaa ttggcgatgt gaccaaaccg ccgctgctgg cacataaagc aatgaaagaa    960
ggcctggtgg ccgcagaaca tgccgcaggt agacctgccg cttttgatca gcagattccg   1020
agtgtggttt ataccagcc ggaatttgca agtgttggta tgaccgaagc agaagcaaaa   1080
gcccgtggcc tggaagtgcg tgtggtcgt tttccgttta gcgcaagcgg tcgcgccctg   1140
accttacaac agaccgaagg tctgattaag ctggttcag atgcagaaaa tgatctgctg   1200
ctgggcgcca atattctggg tcctggtgct agtgatctga tgtgcgaage caccctggca   1260
ctggaaatgg cagccacagc aggtgacctg gcactgacag tgcatccgca tccgaccctg   1320
gcagaaaatc tgatggaagc cgcagaaaat cttcatggcc gtgcaattca tattctgaat   1380
cgc                                                                 1383

SEQ ID NO: 8              moltype = DNA   length = 954
```

```
FEATURE                 Location/Qualifiers
source                  1..954
                        mol_type = genomic DNA
                        organism = Cereibacter sphaeroides
SEQUENCE: 8
atgcgtggta aagcaatggc agaaacccgt catacccgtg tgctgattat tggtagtggc    60
ccggcaggtt ataccgccgc agtttatagt gcacgtgcca tgctgaatcc gctgctgatt   120
cagggtctgc aaccgggtgg tcagctgaca attaccaccg aagtggaaaa ttggccgggt   180
gaccgtgaag tgcagggccc tgagttaatg gttcgtattg aagatcatgc ccgcgcaatg   240
ggtgccgaaa ttgtgagcga ttatattagc agtctggatc tgagtcagcg tccgtttacc   300
gcccgcgcag attcaggtat gacctatacc gcagatgccg ttattctggc caccggcgca   360
caggcacgtt ggctgggttt acctagcgaa gaacgcttta aaggctttgg cgttagtgcc   420
tgtgccacct gcgatggttt ctttttatcgt ggcaaagaag ttgttgtggc cggcggcggt   480
aataccgctg ttgaagaagc actgtttctg accaatttg ccagtaaagt taccctgctg    540
catcgccgtg atagcctgcg tgcagaaaaa attctgcaag atcgtctgtt taagcacccg   600
aaaattgaag tgctgtggaa tcataccatc gaagaagttg ccggcaccga agcaccgctg   660
ggtgtgaccg gtattgttgc acgtaatgtt ctgaccggtg aaaccaccga agttccgtgc   720
gaaggctttt tcgtgccat tggtcatgca ccggccaagc aactggtgaa agatcagctg    780
gaactgcatc atggcggtta tgtgcgtgtg gaacccggca caacccgtac aagtattccg   840
ggtgtttttg cagcaggtga cctgaccgat catgtgtatc gccaggcagt gaccagtgcc   900
ggtatgggtt gcatggccgc tctggatgca gaacgctttc tggcaggcgc ataa         954

SEQ ID NO: 9            moltype = DNA   length = 1347
FEATURE                 Location/Qualifiers
source                  1..1347
                        mol_type = genomic DNA
                        organism = Ectothiorhodospira shaposhnikovii
SEQUENCE: 9
atgaacgacc attacgatct gattgcaatt ggtgccggta cggtggcct gtcagttgtt     60
gaacgcgccg cacgttatgg cgccttatgt gcagttgtgg aaagcggccc gctgggtgt    120
acatgtgtga atgtgggctg tgttccgaaa aaagtgatgt ggtatgcagc cgatatggca   180
catcgcctgg atgatgcccc gggttatggc tttaaactgg cacgtgaagg ttttgattgg   240
agtgaactgg ttggcgcccg tgatgcctat attgaaggca ttaatacctg gtatcacacc   300
tatctggccg atagcggcgt ggatgaaatt ccgggtcgtg cacgcttttgt ggatgcacat   360
accctggaag tggatgcccg tcgtgtgagc gcagatcatg ttgtgattgc cgtgggcggt   420
cagccgagtg ttcctgacat tccgggtgcc gaactgggta ttaccagcga tggcttttc    480
cagctgaaaa gccagccgcg ccgtgttgca gtgattggtg ctggttatat tgcagtggaa   540
ctggccggca tgctgcgcgc attaggtagt gaagtgagca tgtatctgcg ccgtcagacc   600
ctgctgcgca gttttgatcc gatgctgcgt gatacctgat ggaacagat gctggcaatt    660
ggcgttaatc tgtttccgag tacccaggtt ggtcgtctga ttgcccatcc ggatagcgtg   720
gaactgtttt gcgatcaggg cgaatgccgt ggtgtttttg atcaggttat ttgggcaacc   780
ggtcgcaccc cggcaacaaa tgatctggat ctgcataata ccggtattca gccggatgat   840
cagggttata ttccgaccga tctgtatcag aataccggtg gaaggcgt gtatgccatt    900
ggtgacgtta ccggccgtgc ccctctgacc cctgtggcaa tcgcagcagg tcgtcgtctg   960
gcagatcgtc tgtttggtgg tcagaccgat cgccatctga gctatgaaac cattccgagt  1020
gtgattttta gccatccgcc gattggtaca gttggcctga ccgaagaaga gcacgcgcc   1080
gcacatggtg aagcagttaa agtttatagc acccgttta tcagtatgta tcatgccatt   1140
accccgcata aagttgcaac cgccatgaaa ctggtgaccg tgggcgcaca ggaaaaagtg   1200
gtgggtgttc atattattgg tccggatgca gatgaaatgc tgcaaggctt tgccgttgcc  1260
gttcgcatgg gcgcaaccaa acgtgatctg gatgataccc tggcactgca tccgaccagc  1320
gcagaagaac tggtgaccat gaaataa                                      1347

SEQ ID NO: 10           moltype = AA  length = 461
FEATURE                 Location/Qualifiers
source                  1..461
                        mol_type = protein
                        organism = Oceanithermus profundus
SEQUENCE: 10
MYDLIVIGTG PGGYHAAIRA AQLGLKVAAV EAGAVGGVCL NVGCSPTKAL LHAAETLEHA    60
AKGAEFGLVF SEAERDLAKM GRWRDKIVKK LTGGVASLLK GNGVELVKGF ARFTGPRELE   120
VDGKKLEAKK IIVATGSKPA VLPGFEPDGE HVLTSTEMLR VENGVPARLL VIGGGVIGLE   180
FASIYARLGA EVTVVEYEGQ ILPGSDPELV KLLARSLKKQ GIVVKTATKA AGYEKAGGGL   240
RVTVEPAAGG EQEVLDADKI LLAVGRVPFT EGLNLEAAGV RTDERGFVPT NEHLETNVPG   300
VYAIGDVTKP PLLAHKAMKE GLVAAEHAAG RPAAFDQQIP SVVYTQPEFA SVGMTEAEAK   360
ARGLEVRVGR PFPFSASGRAL TLQQTEGLIK LVADAENDLL LGAHILGPGA SDLIAEATLA   420
LEMAATAGDL ALTVHPHPTL AENLMEAAEN LHGRAIHILN R                      461

SEQ ID NO: 11           moltype = AA  length = 461
FEATURE                 Location/Qualifiers
source                  1..461
                        mol_type = protein
                        organism = Oceanithermus profundus
SEQUENCE: 11
MYDLIVIGTG PGGYHAAIRA AQLGLKVAAV EAGAVGGVCL NVGCIPTKAL LHAAETLEHA    60
AKGAEFGLVF SEAERDLAKM GRWRDKIVKK LTGGVASLLK GNGVELVKGF ARFTGPRELE   120
VDGKKLEAKK IIVATGSKPA VLPGFEPDGE HVLTSTEMLR VENGVPARLL VIGGGVIGLE   180
FASIYARLGA EVTVVEYEGQ ILPGSDPELV KLLARSLKKQ GIVVKTATKA AGYEKAGGGL   240
RVTVEPAAGG EQEVLDADKI LLAVGAVPFT EGLNLEAAGV RTDERGFVPT NEHLETNVPG   300
VYAIGDVTKP PLLAHKAMKE GLVAAEHAAG RPAAFDQQIP SVVYTQPEFA SVGMTEAEAK   360
```

```
ARGLEVRVGR FPPFSASGRAL TLQQTEGLIK LVADAENDLL LGAHILGPGA SDLIAEATLA    420
LEMAATAGDL ALTVHPHPTL AENLMEAAEN LHGRAIHILN R                        461

SEQ ID NO: 12           moltype = AA  length = 461
FEATURE                 Location/Qualifiers
source                  1..461
                        mol_type = protein
                        organism = Oceanithermus profundus
SEQUENCE: 12
MYDLIVIGTG PGGYHAAIRA AQLGLKVAAV EAGAVGGVCL NVGCIPTKAL LHAAETLEHA    60
AKGAEFGLVF SEAERDLAKM GRWRDKIVKK LTGGVASLLK GNGVELVKGF ARFTGPRELE    120
VDGKKLEAKK IIVATGSKPA VLPGFEPDGE HVLTSTEMLR VENGVPARLL VIGGGVIGLE    180
FASIYARLGA EVTVVEYEGQ ILPGSDPELV KLLARSLKKQ GIVVKTATKA AGYEKAGGGL    240
RVTVEPAAGG EQEVLDADKI LLAVGRVPFT ENLNLEAAGV RTDERGFVPT NEHLETNVPG    300
VYAIGDVTKP PLLAHKAMKE GLVAAEHAAG RPAAFDQQIP SVVYTQPEFA SVGMTEAEAK    360
ARGLEVRVGR FPPFSASGRAL TLQQTEGLIK LVADAENDLL LGAHILGPGA SDLIAEATLA   420
LEMAATAGDL ALTVHPHPTL AENLMEAAEN LHGRAIHILN R                        461

SEQ ID NO: 13           moltype = AA  length = 461
FEATURE                 Location/Qualifiers
source                  1..461
                        mol_type = protein
                        organism = Oceanithermus profundus
SEQUENCE: 13
MYDLIVIGTG PGGYHAAIRA AQLGLKVAAV EAGAVGGVCL NVGCSPTKAL LHAAETLEHA    60
AKGAEFGLVF SEAERDLAKM GRWRDKIVKK LTGGVASLLK GNGVELVKGF ARFTGPRELE    120
VDGKKLEAKK IIVATGSKPA VLPGFEPDGE HVLTSTEMLR VENGVPARLL VIGGGVIGLE    180
FASIYARLGA EVTVVEYEGQ ILPGSDPELV KLLARSLKKQ GIVVKTATKA AGYEKAGGGL    240
RVTVEPAAGG EQEVLDADKI LLAVGAVPFT EGLNLEAAGV RTDERGFVPT NEHLETNVPG    300
VYAIGDVTKP PLLAHKAMKE GLVAAEHAAG RPAAFDQQIP SVVYTQPEFA SVGMTEAEAK    360
ARGLEVRVGR FPPFSASGRAL TLQQTEGLIK LVADAENDLL LGAHILGPGA SDLIAEATLA   420
LEMAATAGDL ALTVHPHPTL AENLMEAAEN LHGRAIHILN R                        461

SEQ ID NO: 14           moltype = AA  length = 461
FEATURE                 Location/Qualifiers
source                  1..461
                        mol_type = protein
                        organism = Oceanithermus profundus
SEQUENCE: 14
MYDLIVIGTG PGGYHAAIRA AQLGLKVAAV EAGAVGGVCL NVGCSPTKAL LHAAETLEHA    60
AKGAEFGLVF SEAERDLAKM GRWRDKIVKK LTGGVASLLK GNGVELVKGF ARFTGPRELE    120
VDGKKLEAKK IIVATGSKPA VLPGFEPDGE HVLTSTEMLR VENGVPARLL VIGGGVIGLE    180
FASIYARLGA EVTVVEYEGQ ILPGSDPELV KLLARSLKKQ GIVVKTATKA AGYEKAGGGL    240
RVTVEPAAGG EQEVLDADKI LLAVGRVPFT ENLNLEAAGV RTDERGFVPT NEHLETNVPG    300
VYAIGDVTKP PLLAHKAMKE GLVAAEHAAG RPAAFDQQIP SVVYTQPEFA SVGMTEAEAK    360
ARGLEVRVGR FPPFSASGRAL TLQQTEGLIK LVADAENDLL LGAHILGPGA SDLIAEATLA   420
LEMAATAGDL ALTVHPHPTL AENLMEAAEN LHGRAIHILN R                        461

SEQ ID NO: 15           moltype = AA  length = 461
FEATURE                 Location/Qualifiers
source                  1..461
                        mol_type = protein
                        organism = Oceanithermus profundus
SEQUENCE: 15
MYDLIVIGTG PGGYHAAIRA AQLGLKVAAV EAGAVGGVCL NVGCIPTKAL LHAAETLEHA    60
AKGAEFGLVF SEAERDLAKM GRWRDKIVKK LTGGVASLLK GNGVELVKGF ARFTGPRELE    120
VDGKKLEAKK IIVATGSKPA VLPGFEPDGE HVLTSTEMLR VENGVPARLL VIGGGVIGLE    180
FASIYARLGA EVTVVEYEGQ ILPGSDPELV KLLARSLKKQ GIVVKTATKA AGYEKAGGGL    240
RVTVEPAAGG EQEVLDADKI LLAVGAVPFT ENLNLEAAGV RTDERGFVPT NEHLETNVPG    300
VYAIGDVTKP PLLAHKAMKE GLVAAEHAAG RPAAFDQQIP SVVYTQPEFA SVGMTEAEAK    360
ARGLEVRVGR FPPFSASGRAL TLQQTEGLIK LVADAENDLL LGAHILGPGA SDLIAEATLA   420
LEMAATAGDL ALTVHPHPTL AENLMEAAEN LHGRAIHILN R                        461

SEQ ID NO: 16           moltype = AA  length = 461
FEATURE                 Location/Qualifiers
source                  1..461
                        mol_type = protein
                        organism = Oceanithermus profundus
SEQUENCE: 16
MYDLIVIGTG PGGYHAAIRA AQLGLKVAAV EAGAVGGVCL NVGCSPTKAL LHAAETLEHA    60
AKGAEFGLVF SEAERDLAKM GRWRDKIVKK LTGGVASLLK GNGVELVKGF ARFTGPRELE    120
VDGKKLEAKK IIVATGSKPA VLPGFEPDGE HVLTSTEMLR VENGVPARLL VIGGGVIGLE    180
FASIYARLGA EVTVVEYEGQ ILPGSDPELV KLLARSLKKQ GIVVKTATKA AGYEKAGGGL    240
RVTVEPAAGG EQEVLDADKI LLAVGAVPFT ENLNLEAAGV RTDERGFVPT NEHLETNVPG    300
VYAIGDVTKP PLLAHKAMKE GLVAAEHAAG RPAAFDQQIP SVVYTQPEFA SVGMTEAEAK    360
ARGLEVRVGR FPPFSASGRAL TLQQTEGLIK LVADAENDLL LGAHILGPGA SDLIAEATLA   420
LEMAATAGDL ALTVHPHPTL AENLMEAAEN LHGRAIHILN R                        461

SEQ ID NO: 17           moltype = AA  length = 317
```

```
FEATURE                 Location/Qualifiers
source                  1..317
                        mol_type = protein
                        organism = Cereibacter sphaeroides
SEQUENCE: 17
MRGKAMAETR HTRVLIIGSG PAGYTAAVYS ARAMLNPLLI QGLQPGGQLT ITTEVENWPG    60
DREVQGPELM VRMEDHARAM GAEIVSDYIS KLDLSQRPFT ARADSGMTYT ADAVILATGA   120
QARWLGLPSE ERFKGFGVSA CATCDGFFYR GKEVVVAGGG NTAVEEALFL TNFASKVTLV   180
HRRDSLRAEK ILQDRLFKHP KIEVLWNHTI EEVAGTEAPL GVTGIVARNV LTGETTEVPC   240
EGFFVAIGHA PASELVKDQL ELHHGGYVRV EPGTTRTSIP GVFAAGDLTD HVYRQAVTSA   300
GMGCMAALDA ERFLAGA                                                 317

SEQ ID NO: 18           moltype = AA  length = 317
FEATURE                 Location/Qualifiers
source                  1..317
                        mol_type = protein
                        organism = Cereibacter sphaeroides
SEQUENCE: 18
MRGKAMAETR HTRVLIIGSG PAGYTAAVYS ARAMLNPLLI QGLQPGGQLT ITTEVENWPG    60
DREVQGPELM VRMEDHARAM GAEIVSDYIS SLDLSQRPFT ARADSGMTYT ADAVILATGA   120
QARWLGLPSE ERFKGFGVSA CATCDGFFYR GKEVVVAGGG NTAVEEALFL TNFASKVTLV   180
HRRDSLRAEK ILIDRLFKHP KIEVLWNHTI EEVAGTEAPL GVTGIVARNV LTGETTEVPC   240
EGFFVAIGHA PASELVKDQL ELHHGGYVRV EPGTTRTSIP GVFAAGDLTD HVYRQAVTSA   300
GMGCMAALDA ERFLAGA                                                 317

SEQ ID NO: 19           moltype = AA  length = 317
FEATURE                 Location/Qualifiers
source                  1..317
                        mol_type = protein
                        organism = Cereibacter sphaeroides
SEQUENCE: 19
MRGKAMAETR HTRVLIIGSG PAGYTAAVYS ARAMLNPLLI QGLQPGGQLT ITTEVENWPG    60
DREVQGPELM VRMEDHARAM GAEIVSDYIS KLDLSQRPFT ARADSGMTYT ADAVILATGA   120
QARWLGLPSE ERFKGFGVSA CATCDGFFYR GKEVVVAGGG NTAVEEALFL TNFASKVTLV   180
HRRDSLRAEK ILIDRLFKHP KIEVLWNHTI EEVAGTEAPL GVTGIVARNV LTGETTEVPC   240
EGFFVAIGHA PASELVKDQL ELHHGGYVRV EPGTTRTSIP GVFAAGDLTD HVYRQAVTSA   300
GMGCMAALDA ERFLAGA                                                 317

SEQ ID NO: 20           moltype = AA  length = 448
FEATURE                 Location/Qualifiers
source                  1..448
                        mol_type = protein
                        organism = Ectothiorhodospira shaposhnikovii
SEQUENCE: 20
MNDHYDLIAI GAGSGGLSVV ERAARYGALC AVVESGPLGG TCVNVGCVPK KVMWYAADMA    60
HRLDDAPGYG FKLAREGFDW SELVGARDAY IEGINTWYHT YLADSGVDEI PGRARFVDAH   120
TLEVDGRRVS ADHVVIAVGG QPSVPDIPGV ELGITSDGFF QLKSQPRRVA VIGAGYIAVE   180
LAGMLRALGS EVSMYLRRQT LLRSFDPMLR DTLMEQMLAD GVNLFPSTQV GRLIAHPDSV   240
ELFCDQGECR GVFDQVIWAT GRTPATNDLD LHNTGIQPDD QGYIPTDLYQ NTSVEGVYAI   300
GDVTGRAPLT PVAIAAGRRL ADRLFGGQTD RHLSYETIPS VIFSHPPIGT VGLTEEEARA   360
AHGEAVKVYS TRFTSMYHAM TPHKVATAMK LVTGAQEKV VGVHIIGPDA DEMLQGFAVA   420
VRMGATKRDL DDTVALHPTS AEELVTMK                                    448

SEQ ID NO: 21           moltype = AA  length = 448
FEATURE                 Location/Qualifiers
source                  1..448
                        mol_type = protein
                        organism = Ectothiorhodospira shaposhnikovii
SEQUENCE: 21
MNDHYDLIAI GAGSGGLSVV ERAARYGALC AVVESGPLGG TCVNVGCVPK KVMWYAADMA    60
HRLDDAPGYG FKLAREGFDW SELVGARDAY IEGINTWYHT YLADSGVDEI PGRARFVDAH   120
TLEVDGRRVS ADHVVIAVGG QPSVPDIPGA ELGITSDGFF QLKSQPRRVA VIGAGYIAVE   180
LAGMLRALGS EVSMYLRRQT LLRSFDPMLR DTLMEQMLAD GVNLFPSTQV GRLIAHPDSV   240
ELFCDQGECR GVFDQVIWAT GRTPATNDLD LHNTGIQPDD QGYIVTDLYQ NTSVEGVYAI   300
GDVTGRAPLT PVAIAAGRRL ADRLFGGQTD RHLSYETIPS VIFSHPPIGT VGLTEEEARA   360
AHGEAVKVYS TRFTSMYHAM TPHKVATAMK LVTGAQEKV VGVHIIGPDA DEMLQGFAVA   420
VRMGATKRDL DDTVALHPTS AEELVTMK                                    448

SEQ ID NO: 22           moltype = AA  length = 448
FEATURE                 Location/Qualifiers
source                  1..448
                        mol_type = protein
                        organism = Ectothiorhodospira shaposhnikovii
SEQUENCE: 22
MNDHYDLIAI GAGSGGLSVV ERAARYGALC AVVESGPLGG TCVNVGCVPK KVMWYAADMA    60
HRLDDAPGYG FKLAREGFDW SELVGARDAY IEGINTWYHT YLADSGVDEI PGRARFVDAH   120
TLEVDGRRVS ADHVVIAVGG QPSVPDIPGV ELGITSDGFF QLKSQPRRVA VIGAGYIAVE   180
LAGMLRALGS EVSMYLRRQT LLRSFDPMLR DTLMEQMLAD GVNLFPSTQV GRLIAHPDSV   240
ELFCDQGECR GVFDQVIWAT GRTPATNDLD LHNTGIQPDD QGYIVTDLYQ NTSVEGVYAI   300
```

```
GDVTGRAPLT PVAIAAGRRL ADRLFGGQTD RHLSYETIPS VIFSHPPIGT VGLTEEEARA    360
AHGEAVKVYS TRFTSMYHAM TPHKVATAMK LVTVGAQEKV VGVHIIGPDA DEMLQGFAVA    420
VRMGATKRDL DDTVALHPTS AEELVTMK                                      448
```